US010814124B2

(12) United States Patent
Perraud et al.

(10) Patent No.: US 10,814,124 B2
(45) Date of Patent: Oct. 27, 2020

(54) ELECTRICAL CONNECTOR, IN PARTICULAR FOR A CUTANEOUS DEVICE

(71) Applicant: COMMISSARIAT A L'ENERGIE ATOMIQUE ET AUX ENERGIES ALTERNATIVES, Paris (FR)

(72) Inventors: Simon Perraud, Bandol (FR); Fabrice Emieux, Voreppe (FR); Nicolas Karst, Folkling (FR); Philippe Pantigny, Claix (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 16/246,309

(22) Filed: Jan. 11, 2019

(65) Prior Publication Data

US 2019/0143096 A1 May 16, 2019

Related U.S. Application Data

(62) Division of application No. 15/311,802, filed as application No. PCT/IB2015/053484 on May 12, 2015, now Pat. No. 10,213,594.

(30) Foreign Application Priority Data

May 19, 2014 (FR) ..................................... 14 54451

(51) Int. Cl.
*A61N 1/04* (2006.01)
(52) U.S. Cl.
CPC ........... *A61N 1/048* (2013.01); *A61N 1/0476* (2013.01); *A61N 1/0492* (2013.01)

(58) Field of Classification Search
CPC ..... A61N 1/048; A61N 1/0476; A61N 1/0492
(Continued)

(56) References Cited

U.S. PATENT DOCUMENTS 4,025,964 A * 5/1977 Owens .............. A61M 39/0247
623/11.11
4,479,685 A * 10/1984 Kirby ..................... H01R 11/30
367/153
(Continued)

FOREIGN PATENT DOCUMENTS

FR 2991589 12/2013

OTHER PUBLICATIONS

Rapport de Recherche Préliminaire dated Nov. 18, 2014, issued in priority French Application No. 1454451, filed May 19, 2014, 1 page.
(Continued)

*Primary Examiner* — Alexander Gilman
(74) *Attorney, Agent, or Firm* — Christensen O'Connor Johnson Kindness PLLC

(57) ABSTRACT

An electrical connector, in particular for a medical device that is intended to be secured to the skin of a user, the connector comprising a base intended to be solidly connected to the device and a plug intended to be solidly connected to an electric conductor, wherein the plug comprises a connection means and the base comprises a plurality of connection means, each being adapted to engage with the connection means of the plug in order to establish a connection between the base and the plug comprising a base secured to the device and a plug configured to be secured to an electrical conductor, wherein the base includes a plurality of protuberances and the plug includes a cavity.

6 Claims, 20 Drawing Sheets

(58) Field of Classification Search
USPC .......................................................... 439/660
See application file for complete search history.

(56) References Cited

U.S. PATENT DOCUMENTS

| | | | | |
|---|---|---|---|---|
| 5,355,883 | A * | 10/1994 | Ascher | A61B 5/0416 439/488 |
| 5,415,164 | A * | 5/1995 | Faupel | A61B 5/04 600/372 |
| 5,660,177 | A * | 8/1997 | Faupel | A61B 5/04 600/382 |
| 5,697,369 | A * | 12/1997 | Long, Jr. | A61B 5/04 600/407 |
| 5,823,957 | A * | 10/1998 | Faupel | A61B 5/04087 600/397 |
| 7,107,104 | B2 * | 9/2006 | Keravel | A61N 1/0531 600/377 |
| 8,131,375 | B2 * | 3/2012 | Greenberg | A61F 9/08 607/54 |
| 8,214,057 | B2 * | 7/2012 | Barolat | A61B 5/04001 607/117 |
| 9,391,394 | B2 * | 7/2016 | Kockx | A61N 1/048 |
| 9,968,772 | B2 * | 5/2018 | Kockx | H01R 13/506 |
| 10,213,594 | B2 * | 2/2019 | Perraud | A61N 1/0476 |
| 2002/0128700 | A1 | 9/2002 | Cross, Jr. | A61N 1/0529 607/117 |
| 2003/0195587 | A1 * | 10/2003 | Rigaux | A61N 1/0452 607/48 |
| 2004/0002647 | A1 * | 1/2004 | Desai | A61B 8/0841 600/417 |
| 2004/0176675 | A1 * | 9/2004 | Rice | A61B 5/04 600/393 |
| 2005/0215872 | A1 * | 9/2005 | Berner | A61B 5/14532 600/347 |
| 2007/0026695 | A1 * | 2/2007 | Lee | H01R 12/592 439/37 |
| 2007/0072442 | A1 * | 3/2007 | DiFonzo | H01R 13/6205 439/39 |
| 2009/0306741 | A1 | 12/2009 | Hogle et al. | |
| 2011/0171837 | A1 * | 7/2011 | Hardisty | H01R 13/6205 439/39 |
| 2012/0294474 | A1 * | 11/2012 | Wu | H02K 35/02 381/400 |
| 2013/0023816 | A1 * | 1/2013 | Bachinski | A61N 1/36014 604/20 |
| 2013/0066412 | A1 * | 3/2013 | Van Der Beek | A61N 1/048 607/152 |
| 2016/0000548 | A1 * | 1/2016 | Aiden | A61F 2/0059 623/23.72 |

OTHER PUBLICATIONS

International Search Report dated Aug. 6, 2015, issued in corresponding International Application No. PCT/IB2015/053484, filed May 12, 2015, 3 pages.
Written Opinion of the International Searching Authority dated Aug. 6, 2015, issued in corresponding International Application No. PCT/IB2015/053484, filed May 12, 2015, 6 pages.
International Preliminary Report on Patentability dated Nov. 22, 2016, issued in corresponding International Application No. PCT/IB2015/053484, filed May 12, 2015, 1 page.

* cited by examiner

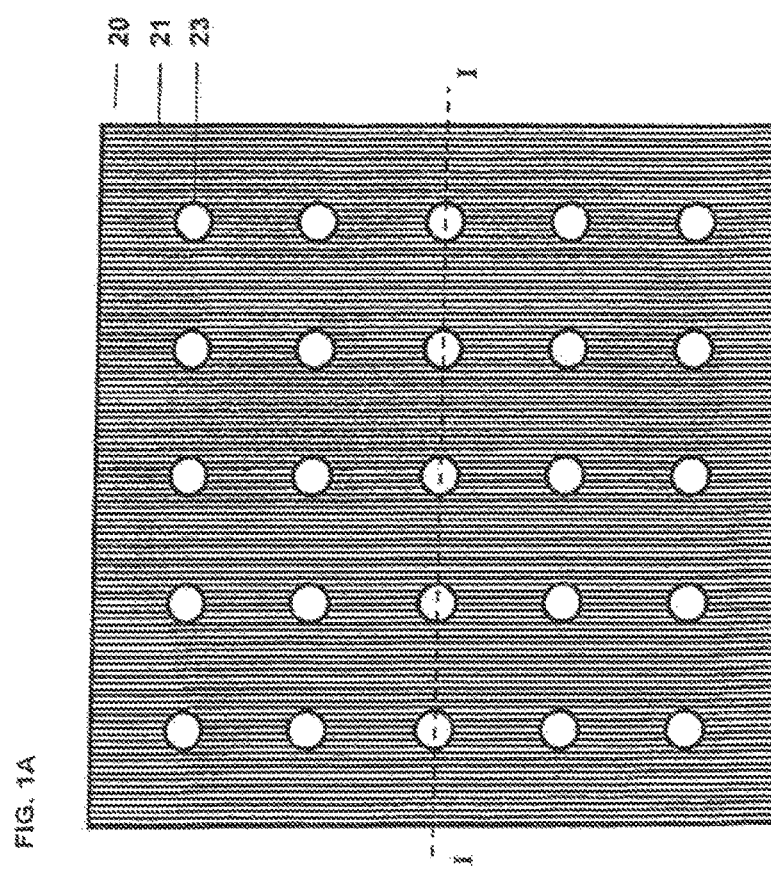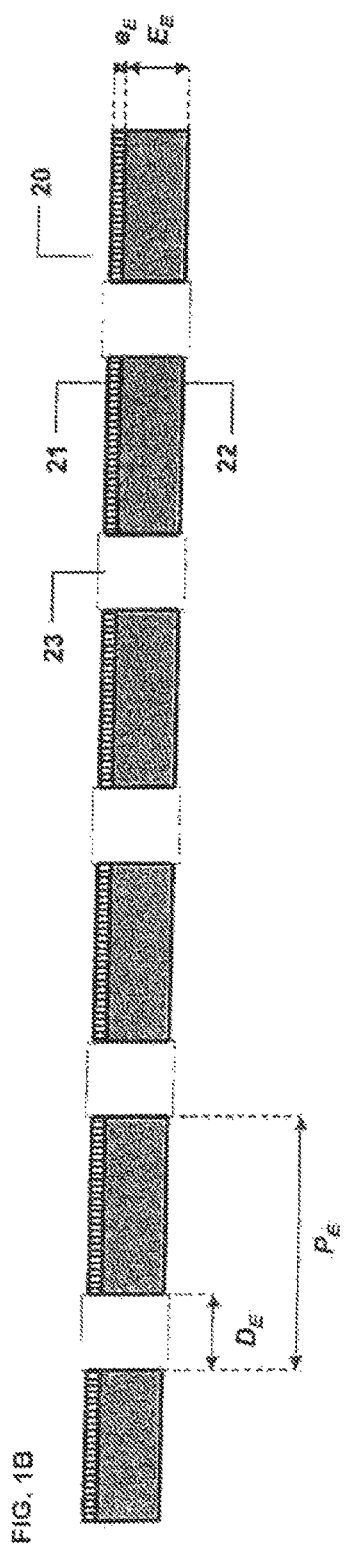

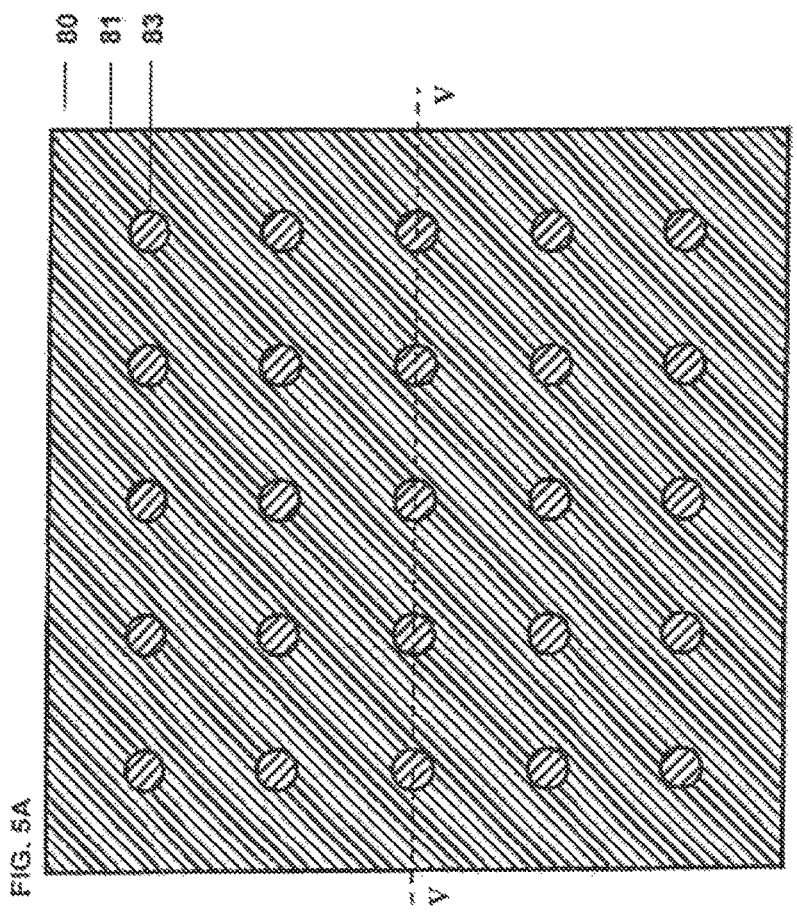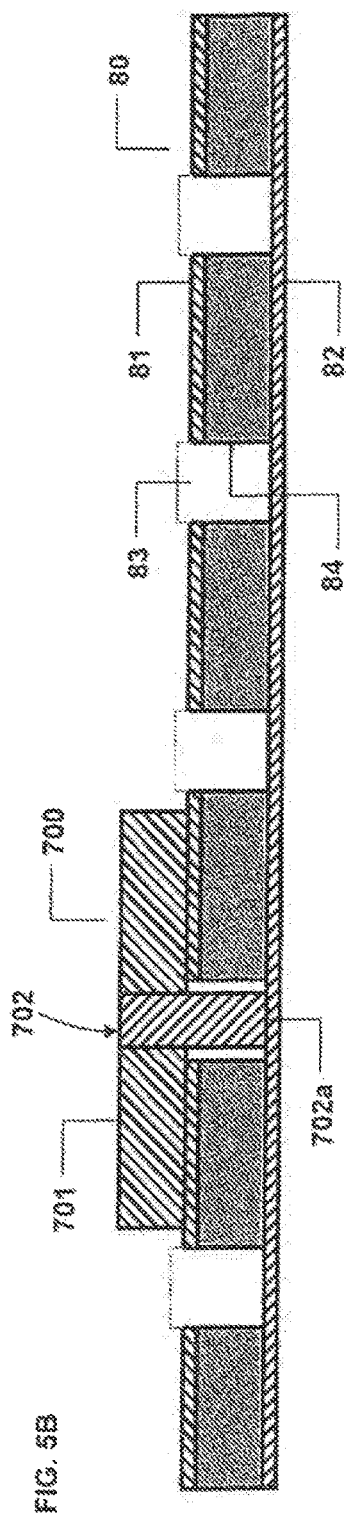

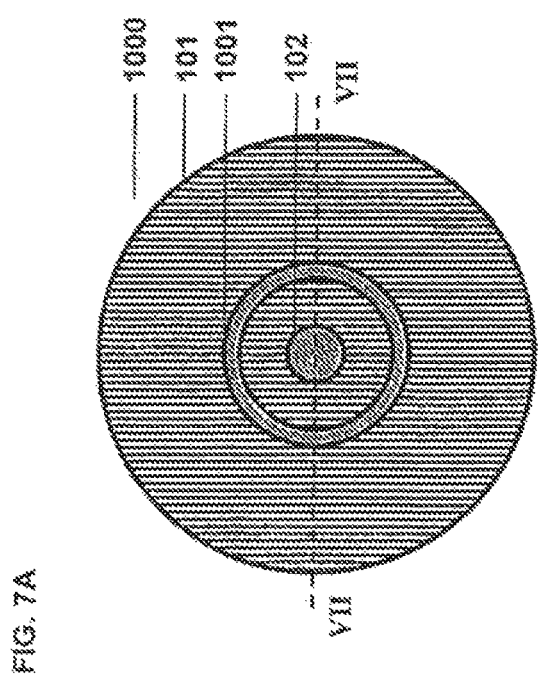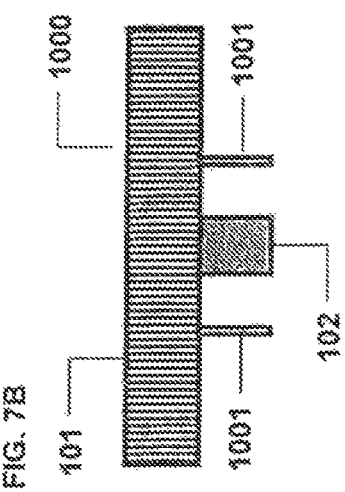
FIG. 7A  FIG. 7B
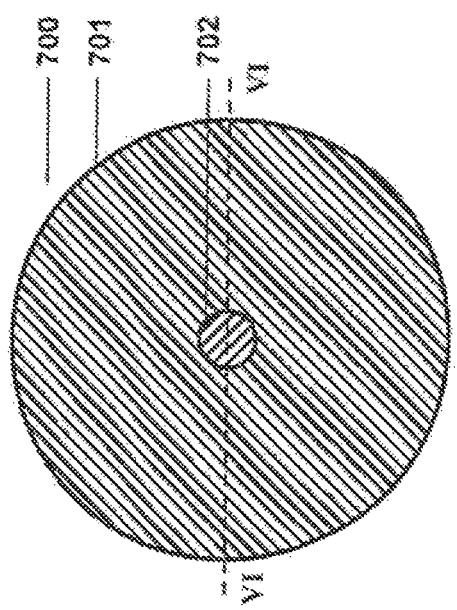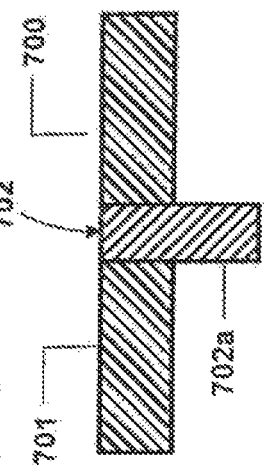
FIG. 6A  FIG. 6B

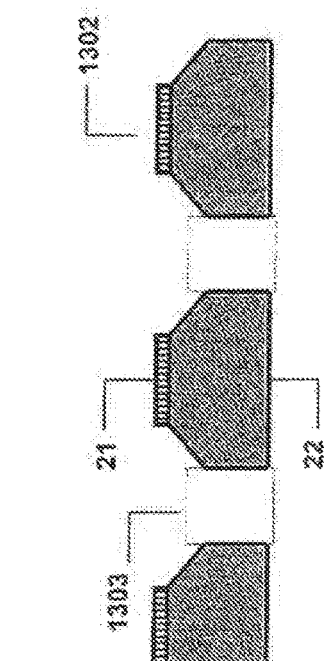
FIG. 10
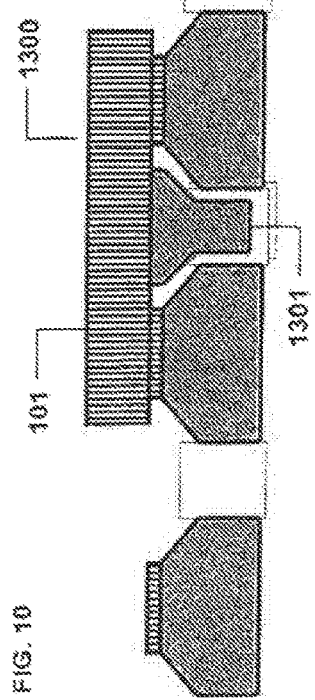
FIG. 9
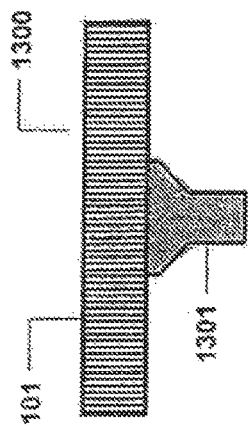
FIG. 11
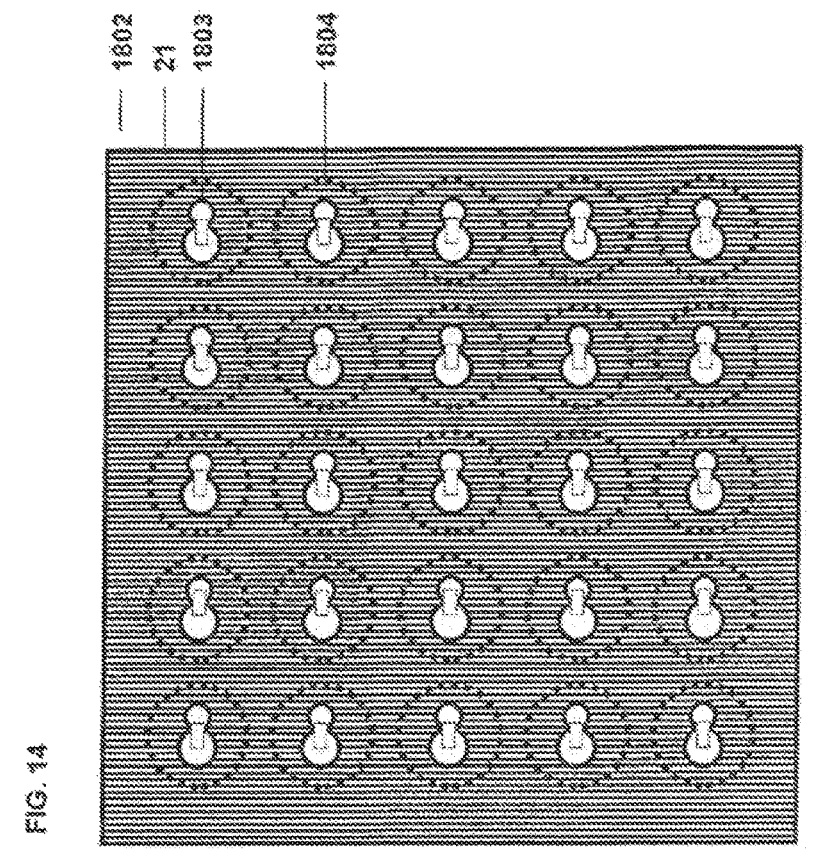
FIG. 14
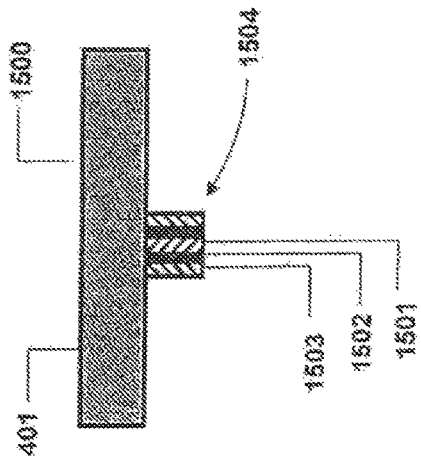

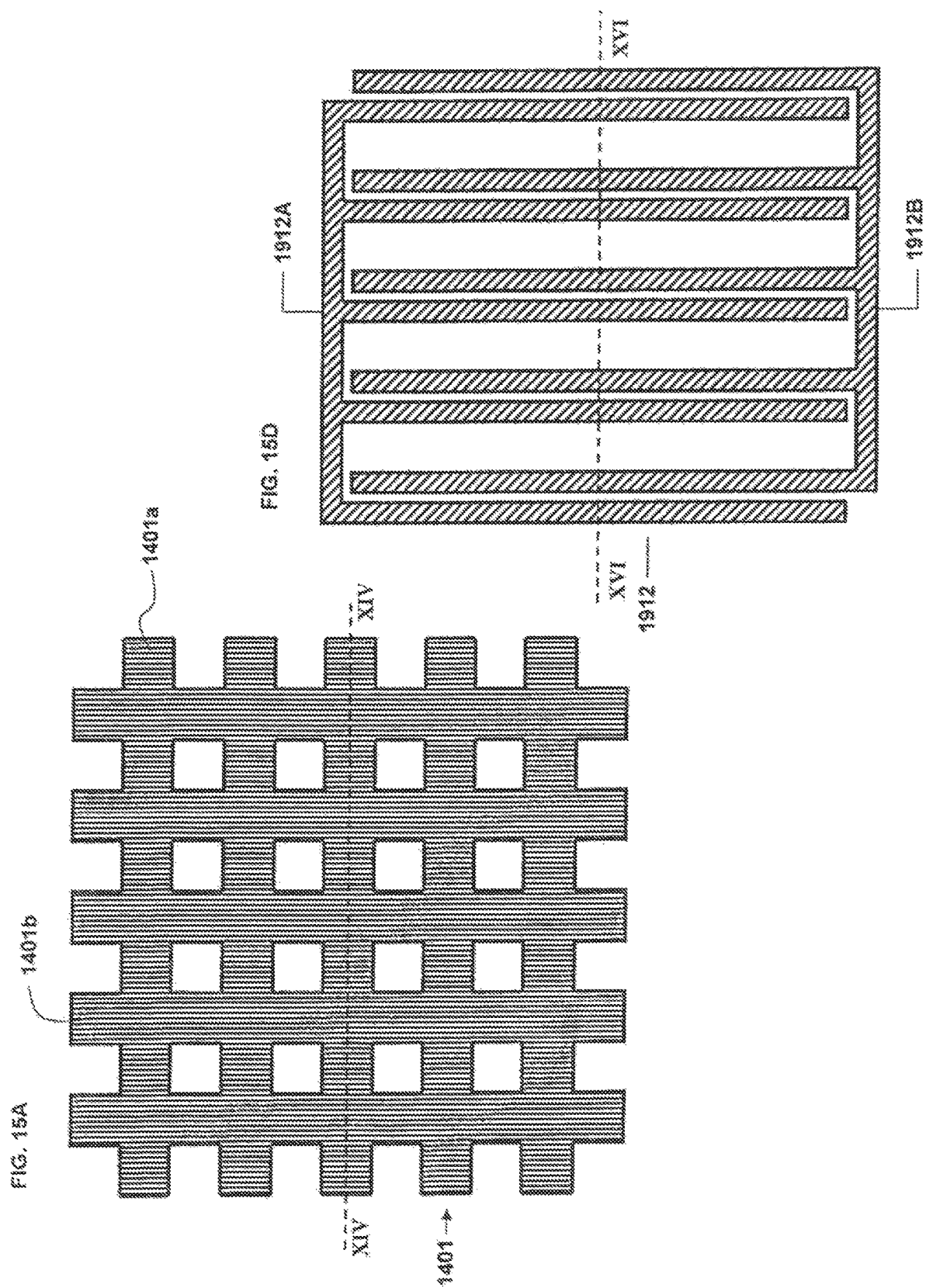

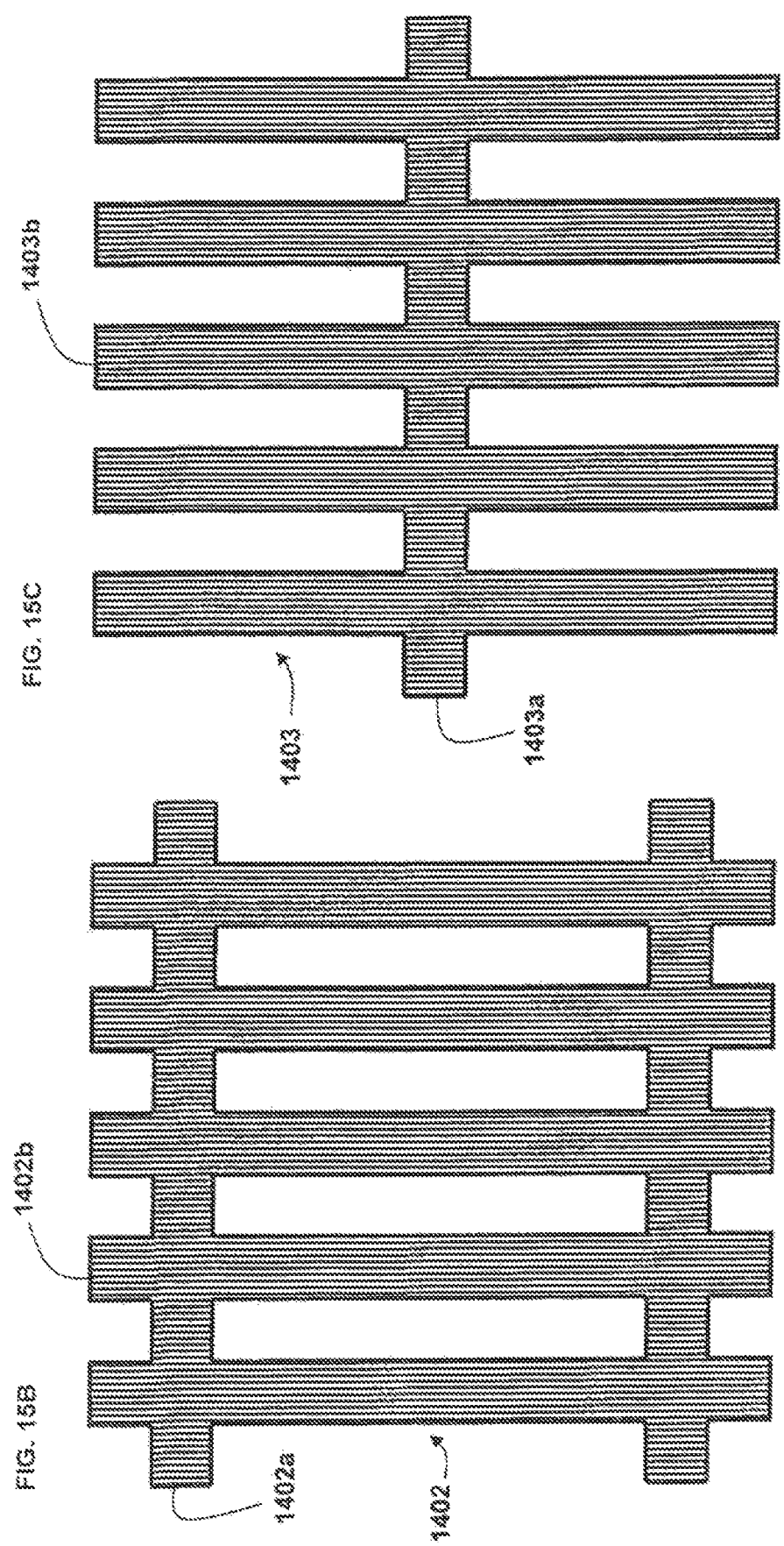

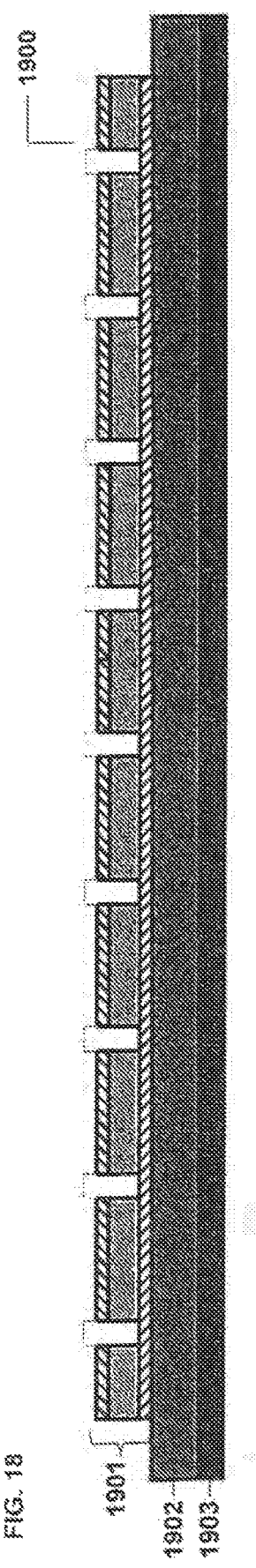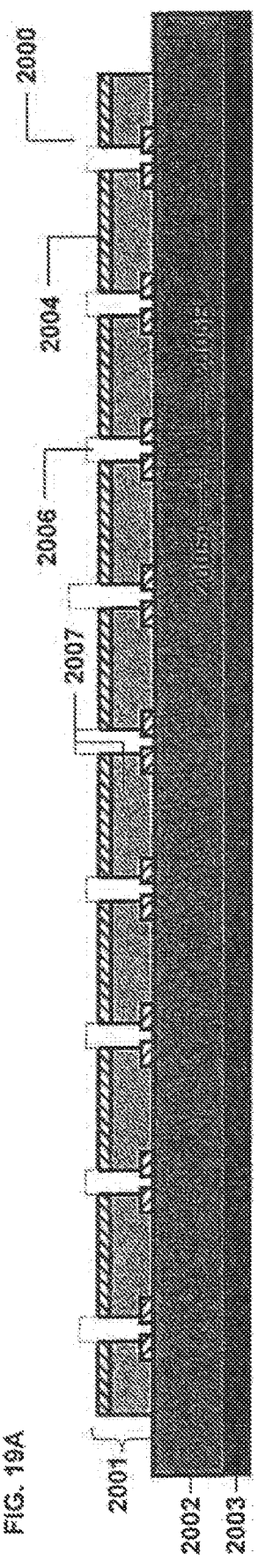
FIG. 18
FIG. 19A

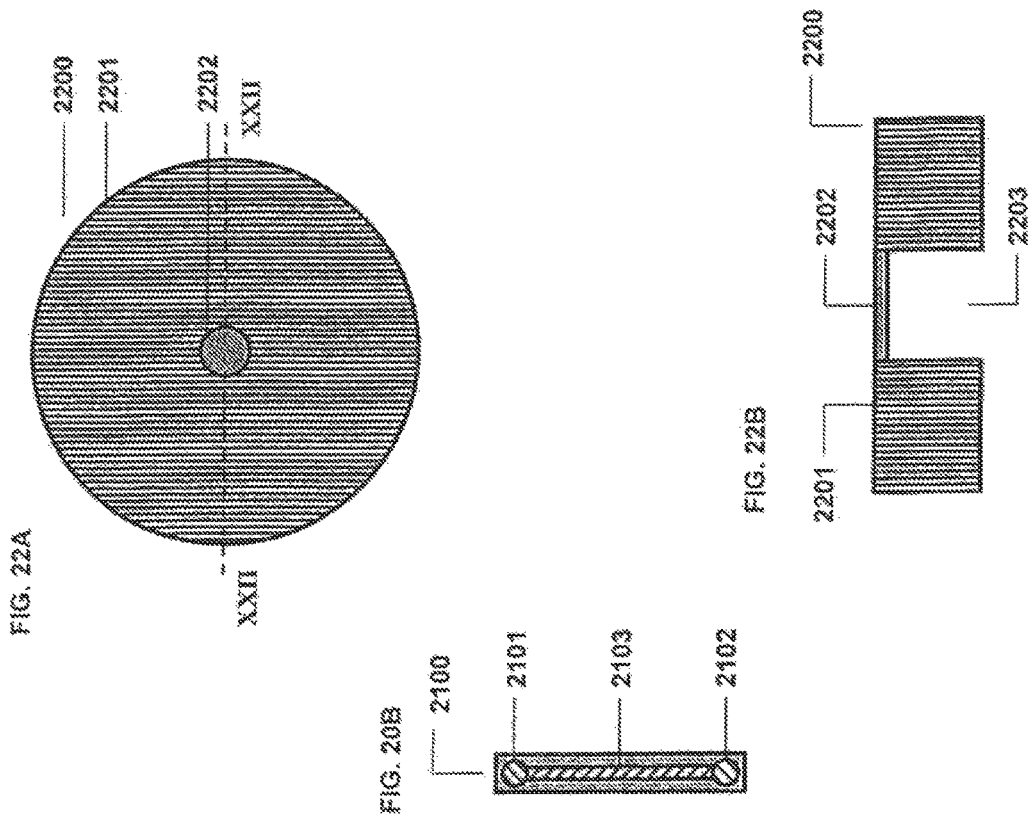

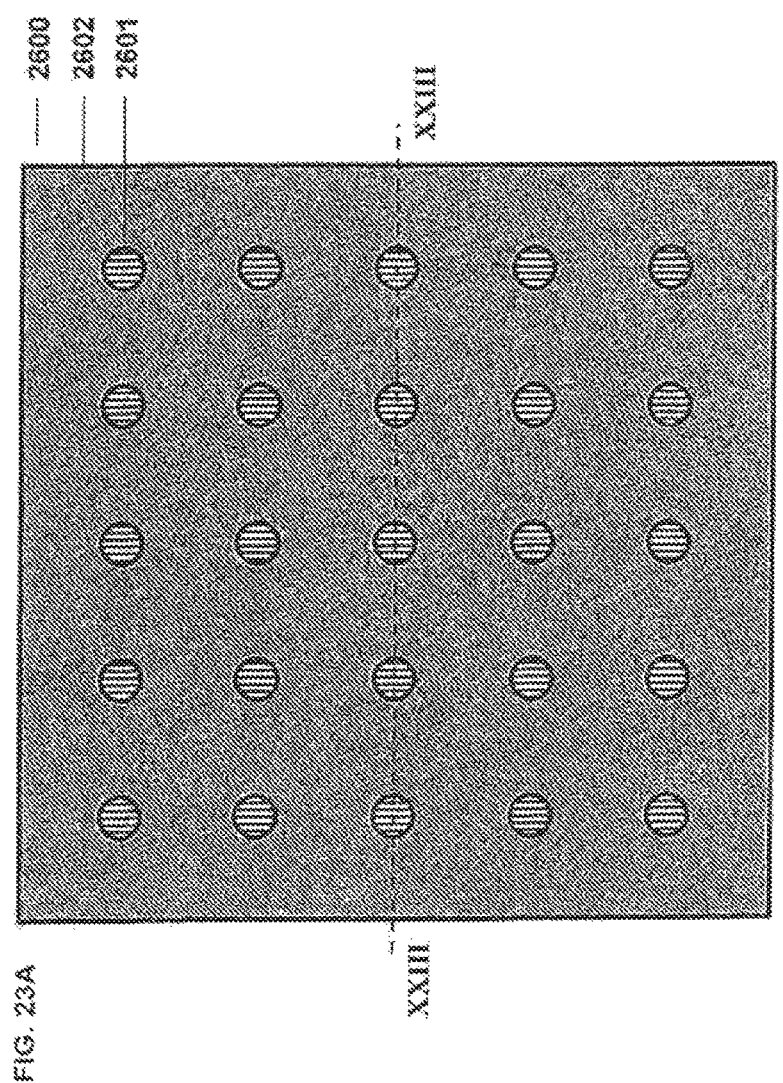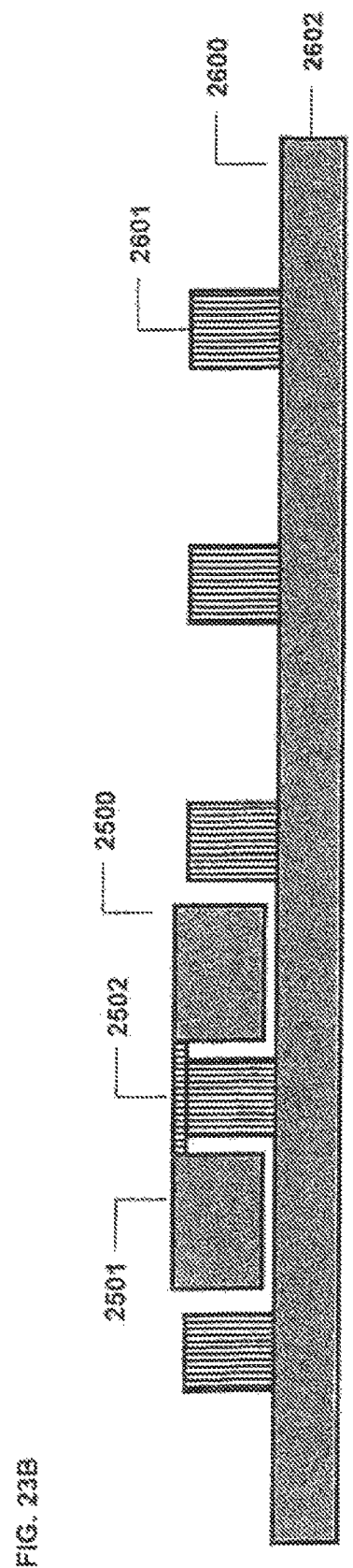
FIG. 23A
FIG. 23B

ELECTRICAL CONNECTOR, IN PARTICULAR FOR A CUTANEOUS DEVICE

FIELD OF THE DISCLOSURE

Embodiments of the current disclosure relate to the technical field of devices intended to be fixed on the skin of a user.

It in particular involves medical devices, such as cutaneous electrodes for measuring physiological parameters or impulse generators for electrostimulation.

BACKGROUND

These devices are generally compact enough to be placed directly on a user's skin. They are designed also to be relatively thin and flexible.

These devices generally comprise an electrical connector making it possible to connect the device to an electrical wire.

The electrical connector is made up of two parts:

a plug, i.e., the part of the connector situated at the end of the electrical wire, a base, i.e., the part of the connector secured to the device.

One commonly used electrical connector is of the "pushbutton" type. Generally, the plug comprises a cavity (female plug) and the base comprises a protuberance (male base) intended to be inserted into the cavity.

Electrical connectors of the pushbutton type have drawbacks, in particular when the user fastens the device on his skin before performing the connection.

Indeed, pressure (i.e., a force perpendicular to the plane of the device) must be exerted to perform the connection, which may be painful for the user.

Furthermore, the user must position the cavity of the plug exactly opposite the protuberance of the base before exerting the pressure. Thus, a visual inspection is necessary to make the connection quickly. As a result, making the connection may become an extremely long and tedious operation if this visual inspection is not possible. This for example occurs when the user has fixed the device on his back or behind one of his legs.

Thus, with an electrical connector of the pushbutton type, it is generally preferable to fix the device on the skin after having performed the electrical connection, which is less practical for the user.

Other types of connection have been proposed in the prior art.

In particular, electrical connectors comprising magnetic parts are described in document U.S. Pat. No. 4,112,941.

This document specifically relates to the field of cutaneous electrodes, with a plug comprising a cavity (female plug) and a base comprising a protuberance (male base). With the electrical connector described in this document, it is no longer necessary to exert pressure to perform the connection, since the magnetic force between the plug and the base suffices to insert the protuberance of the base into the cavity of the plug. This therefore resolves one of the problems encountered with connectors of the pushbutton type, since it is no longer necessary to exert pressure to make the connection.

However, a visual inspection is still necessary to perform the connection quickly. Indeed, the user must at least preposition the cavity of the plug near the protuberance of the base, before the magnetic forces begin to act and assemble the two parts of the connector.

SUMMARY

Embodiments of the current disclosure aim to offset these drawbacks by proposing an electrical connector, in particular for a medical device intended to be fixed on the skin of a user, comprising a base secured to the device and a plug intended to be secured to an electrical conductor, which makes it possible to perform a quick connection of the base and the plug without visual inspection, and preferably without exerting pressure.

According to the disclosure, the plug comprises a connection means and the base comprises a plurality of connection means, each of them being suitable for cooperating with the connecting means of the plug to ensure the connection between the base and the plug.

Thus, the base includes a high density of potential connection zones with the plug, which makes it possible to perform a quick connection between the base and the plug, with no visual inspection.

Preferably, the center-to-center distance between two adjacent connecting means of the base is comprised between 1.5 and 10 times the section of these connecting means.

Furthermore, the connecting means of the base are preferably distributed uniformly over the surface of the base.

The electrical connector according to the disclosure preferably includes magnetic means on both the plug and the base.

The presence of these magnetic means prevents the user from having to exert pressure to make the connection between the plug and the base.

They therefore contribute to facilitating the connection between the plug and the base, with no visual inspection.

In a first embodiment, the base includes a plurality of holes and the plug includes a protuberance.

In this first embodiment of the connector, the base is made up of a stack of at least two layers, one of them performing at least a mechanical support function and the at least two layers also performing an electrical function and optionally a magnetic function, the holes of the base traversing at least the layer acting as mechanical support, and the plug comprising a base and a protuberance performing an electrical function and optionally a magnetic function.

In a first form of the embodiment, the stack making up the base comprises a layer performing a mechanical support function and a layer performing an electrical function and optionally a magnetic function, the holes traversing the stack.

Furthermore, the electrical function and optionally magnetic function of the plug is performed by the base.

In a second form of the first embodiment of the connector, the stack making up the base comprises a layer performing an electrical function and a layer performing a mechanical function, the layer performing an electrical function also being able to perform a magnetic function, the holes only traversing the layer performing a mechanical function, the electrical function and optionally magnetic function of the plug being performed by the protuberance.

In a third form of the first embodiment of the connector, the stack making up the base successively comprises a layer performing an electric function, a layer performing a mechanical function and optionally a layer performing a magnetic function, the holes traversing the layer performing a magnetic function and, when it is present, the layer performing a magnetic function, any magnetic function of the plug being performed by the base and the electrical function of the plug being performed by the protuberance.

In a first particular configuration, the potential magnetic function is performed by the layer performing a magnetic function.

In a second particular configuration, a layer having an aesthetic function is provided on the layer performing a mechanical function or on the potential layer performing a magnetic function.

In a first alternative embodiment, the plug comprises an annular part protruding on the base and extending around the protuberance, the base comprising, around each hole, an annular opening to receive the protruding annular part of the plug.

In a second alternative embodiment, the plug includes a protuberance having a flared shape becoming narrower as it moves away from the base, the holes of the base including a corresponding shape to receive this protuberance.

In a third alternative embodiment, the protuberance of the plug comprises two parts performing an electrical function and optionally a magnetic function, separated by an insulator.

In a fourth alternative embodiment, the protuberance of the plug has a flared shape becoming wider as it moves away from the base, the holes of the base having a corresponding shape to receive this protuberance.

In a fifth alternative, the layer of the base that is not traversed by the holes is a discontinuous layer, in particular assuming the form of a grid or independent parts that are not electrically connected.

The fifth alternative embodiment is applicable to the second and third forms of the first embodiment of the connector.

The sixth alternative embodiment is applicable to the first and third forms of the first embodiment.

In this sixth alternative, a layer traversed by the holes is a discontinuous layer.

In a seventh alternative embodiment, the protuberance of the plug performs an elastic function to establish better electrical contact.

In an eighth alternative applicable to the second and third forms, the layer performing an electrical function is made up of two separate parts that are not electrically connected, the protuberance or the base of the plug making it possible to electrically connect these two parts when the plug is connected to the base.

In a second embodiment, the base includes a plurality of protuberances and the plug includes a cavity.

In this case, the base comprises at least one layer performing a mechanical support function and the plurality of protuberances is made directly on the mechanical support layer or on an intermediate layer, the protuberances, the layer performing a mechanical support function or the intermediate layer performing an electrical function and optionally a magnetic function, and the plug comprises a cylindrical part defining the cavity that is closed by a base, the electrical function of the plug being performed by the cylindrical part or the base and the potential magnetic function of the plug being performed by the cylindrical part or the base.

In a first form of this second embodiment of the connector, the base comprises, on the layer performing a mechanical support function, a potential intermediate layer, the electrical function and the potential magnetic function being performed by the layer performing a mechanical support function or the potential intermediate layer, the protuberances being made on the layer performing a mechanical support function or on the intermediate layer, the electrical function and the potential magnetic function of the plug being performed by the cylindrical part.

In a second form of the embodiment, the base comprises, on the layer performing a mechanical support function, protuberances made directly on this mechanical support layer, these protuberances performing an electrical function and optionally a magnetic function, the electrical function and the potential magnetic function of the plug being performed by the base.

In a third form of the second embodiment of the connector, the base comprises, on the layer performing a mechanical support function, an intermediate layer performing an electrical function, the protuberances being made on this intermediate layer and optionally performing a magnetic function, the cylindrical part of the plug performing an electrical function and its base optionally performing a magnetic function.

In one alternative of this third form, it is the protuberances that perform an electrical function and the intermediate layer that optionally performs a magnetic function.

The connector according to the disclosure may include a plurality of plugs, the number of which is strictly smaller than that of the connecting means of the base.

The disclosure also relates to a medical device intended to be fixed on the skin of a user, of the patch type.

In this case, the connecting means of the base are advantageously distributed so as to occupy more than 1% of the total surface area of the device, and in particular more than 5% of this surface area.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

FIG. 1 (1A-1B) comprises a top view (FIG. 1A) and a sectional view (FIG. 1B) of a female base corresponding to a first embodiment of the connector, FIG. 2 (2A-2F) shows, in top view (FIGS. 2A, 2C, 2E) and sectional view (FIGS. 2B, 2D, 2F), three examples of male plugs adapted to the base illustrated in FIG. 1, the base according to FIG. 1 being illustrated in dotted lines in FIGS. 2B to 2F, FIG. 3 (3A-3B) shows a top view (FIG. 3A) and a sectional view (FIG. 3B) of a female base corresponding to a second form of the embodiment of the connector according to the disclosure, FIG. 4 (4A-4F) shows top views (FIGS. 4A, 4C, 4E) and sectional views (FIGS. 4B, 4D, 4F) of examples of male plugs adapted to the base illustrated in FIG. 3, the space being partially illustrated in dotted lines in FIGS. 4B, 4D and 4F, FIG. 5 (5A-5B) comprises a top view (FIG. 5A) and a sectional view (FIG. 5B) of a female base corresponding to a third form of the embodiment of the connector, and adapted to the male plug illustrated in FIG. 6, FIG. 6 (6A-6B) comprises a top view (FIG. 6A) and a sectional view (FIG. 6B) of the example of the male plug adapted to the base illustrated in FIG. 5, FIG. 7 (7A-7B) comprises a top view (FIG. 7A) and a sectional view (FIG. 7B) of a first alternative embodiment of a male plug adapted to the bases illustrated in FIGS. 1, 3 and 5, FIG. 8 (8A-8B) comprises a top view (FIG. 8A) and a sectional view (FIG. 8B) of a female base of the type illustrated in FIG. 1 and adapted to the alternative of the plug illustrated in FIG. 7, the plug illustrated in FIG. 7 being shown connected to the base in FIG. 8B, FIG. 9 is a sectional view of a second alternative of a male plug, intended to be connected to a female base of the type illustrated in FIGS. 1, 3 and 5, FIG. 10 is a sectional view of a female base of the type illustrated in FIG. 1, adapted to the plug illustrated in FIG. 9, this plug also being illustrated connected to this base, FIG. 11 is a sectional view illustrating a third alternative embodiment of the male plug adapted to one of the female bases illustrated in one of FIG. 3 or 5, FIG. 12 (12A-12B) comprises a top view (FIG. 12A) and a sectional view (FIG. 12B) of a base of the type illustrated in FIG. 3 and adapted to the plug illustrated in FIG. 11, FIG. 14 is a top view of a base of the type illustrated in FIG. 1 and adapted to the plug illustrated in FIG. 3, FIG. 15 (15A-15E) shows top views of examples of the lower layer of a female base, as illustrated in FIGS. 3 and 5, corresponding to a fifth alternative embodiment, FIG. 18 is a sectional view of a cutaneous electrode comprising a base according to FIG. 5, FIG. 19 (19A-19B) comprises a sectional view (FIG. 19A) of a patch generating impulses and including a base according to FIG. 15D and a top view (FIG. 19B) of the electrical diagram of the patch illustrated in FIG. 19A, FIG. 20 (20A-20B) comprises FIG. 20A showing the devices illustrated in FIGS. 18 and 19 in place on a user's body, the electrode according to FIG. 18 and the patch according to FIG. 19 on the body of a user and FIG. 20B illustrating the elastic band connecting these two devices, FIG. 21 (21A-21B) illustrates a first form of the embodiment of a male base shown in top view (FIG. 21A) and in sectional view (FIG. 21B), FIG. 22 (22A-22B) shows a top view (22A) and a sectional view (22B) of the female plug adapted to the base illustrated in FIG. 21, FIG. 23 (23A-23B) illustrates a second form of the embodiment of a male base, FIG. 23A illustrating this base seen from above and FIG. 23B illustrating it in sectional view, FIG. 24 (24A-24B) shows a top view (24A) and a sectional view (FIG. 24B) of the female plug adapted to the base illustrated in FIG. 23, FIG. 25 (25A-25B) illustrates a third form of the embodiment of a male base, seen from above (FIG. 25A) and in sectional view (FIG. 25B), FIG. 26 (26A-26B) shows a top view (FIG. 26A) and a sectional view (FIG. 26B) of a female plug adapted to the male base illustrated in FIG. 25.

DETAILED DESCRIPTION

Figure 2A:
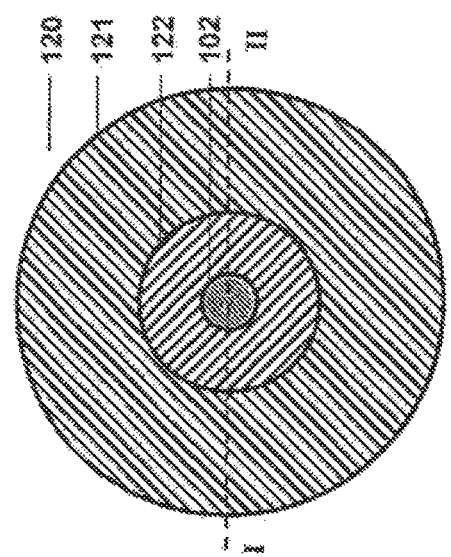

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

FIGS. 1 to 6 illustrate several forms of an embodiment of a connector according to the disclosure including a female base with a plurality of holes and a male plug with a protuberance.

Thus, FIGS. 1 and 2 illustrate a first form of an embodiment of such a connector in which the base comprises:
an upper layer having an electrical and magnetic function,
a lower layer having a mechanical function,
a plurality of holes traversing the upper layer and the lower layer.

FIGS. 3 and 4 illustrate a second form of such a connector in which the base comprises:
an upper layer having a mechanical function,
a lower layer having an electrical and magnetic function,
a plurality of holes traversing only the upper layer.

FIGS. 5 and 6 illustrate a third form of such a connector in which the base comprises:
an upper layer having a magnetic function,
an intermediate layer having a mechanical function,
a lower layer having an electrical function,
a plurality of holes traversing only the upper layer and the intermediate layer.

A first configuration of this third form of the embodiment (not illustrated in the FIGURES) consists of eliminating the upper layer, the potential magnetic function being performed by the intermediate layer.

A second configuration of this third form (not illustrated in the FIGURES) consists of adding a layer, in particular having an aesthetic function, above the layer having a magnetic function. Thus, the base then comprises four layers:
a layer having an aesthetic function,
a layer having a magnetic function,
a layer having a mechanical function,
a layer having an electrical function,
a plurality of holes traversing only the layer having an aesthetic function, the layer having a magnetic function and the layer having a mechanical function.

When the layer having a mechanical function also has a magnetic function, the layer having an aesthetic function is provided directly on this layer.

In each of these three forms:

The layer of the base having an electrical function is intended to establish electrical contact with the part of the plug having an electrical function.

The layer of the base having an electrical function is made from an electrically conductive material and for example a metal, such as copper, silver, gold, aluminum, iron or steel; or a polymer filled with carbon black or metal elements; or a conductive textile material.

Advantageously, it is a thin, or even flexible, layer.

If the layer is made from a metal or a metal alloy, the thickness of the layer is advantageously comprised between 0.001 mm and 1 mm, and preferably between 0.01 mm and 0.2 mm. If the layer is made from a polymer filled with carbon black or metal elements, or a conductive textile material, the thickness of the layer is advantageously comprised between 0.1 mm and 5 mm, and preferably between 0.5 mm and 2 mm.

The layer of the base having a magnetic function and the part of the plug having a magnetic function are intended to exert an attractive magnetic force on one another.

The layer of the base having a magnetic function is made from a ferromagnetic material, for example iron, magnetic steel, cobalt, nickel, or polymer filled with ferromagnetic elements or a magnetized material, for example aluminum-nickel-cobalt, samarium-cobalt, neodyme-iron-boron, or a polymer filled with magnetized elements.

Advantageously, it is a thin, or even flexible, layer.

If the layer of the base is made from a metal or an alloy of metals, the thickness of the layer is advantageously comprised between 0.001 mm and 1 mm, preferably between 0.1 mm and 0.2 mm. If the layer is made from a polymer filled with their magnetic or magnetized elements, the thickness of the layer is advantageously comprised between 0.1 mm and 5 mm, and preferably between 0.5 mm and 2 mm.

The layer of the base having the mechanical function is traversed by the holes.

Any one of these holes is intended to receive the protuberance of the plug and to thereby prevent accidental disconnection via lateral forces, i.e., forces in the plane of the base.

The layer of the base having a mechanical function is thick enough to ensure the lateral maintenance of the protuberance and therefore of the plug.

Advantageously, the thickness of the layer is comprised between 0.1 mm and 5 mm, and preferably between 0.5 mm and 2 mm.

Advantageously, the layer is formed from a very flexible material (for example, a polymer or a textile material), in order to remain flexible despite its relatively significant thickness.

The surface density of holes on the base is high enough to allow a fast connection without visual inspection.

This is facilitated by the action of the magnetic forces. However, this density of holes makes it possible to obtain a connection with no visual inspection, even in the absence of parts performing a magnetic function inside the connector.

However, in the presence of parts performing a magnetic function, one can see that a small lateral movement of the plug near the surface of the base suffices for the magnetic forces to become active and assemble the two parts of the connector, causing the insertion of the protuberance of the plug in one of the holes of the base.

In other words, the high surface density of potential connection zones (the holes of the base), combined with the action of the magnetic forces, makes a connection with no visual inspection even faster and easier.

Advantageously, the diameter of the holes (considering cylindrical holes) is comprised between 0.1 mm and 10 mm, and preferably between 0.5 mm and 5 mm. Advantageously, the center-to-center distance between two adjacent holes with an identical diameter is comprised between 1.5 times the diameter of a hole and 10 times the diameter, preferably between 1.5 times the diameter and 5 times the diameter. The holes do not necessarily have a circular shape, but may for example be oblong.

Advantageously, the holes of the base are distributed uniformly over the surface of the base.

If the base is intended for a device worn in the form of a patch, the sum of the surface areas occupied by the holes advantageously corresponds to more than 1% of the total surface area of the patch, and preferably more than 5% of the total surface area of the patch.

Furthermore, in all of these forms, the plug comprises:
a part serving as a protuberance,
a part having an electrical function (i.e., a part made from an electrically conductive material, for example a metal, such as copper, silver, gold, aluminum, iron or steel; or polymer filled with carbon black or metallic elements),
a part having a magnetic function (i.e., a part made from a ferromagnetic material, for example iron, magnetic steel, cobalt, nickel; or a part made from a magnetized material, for example ferrite, aluminum-nickel-cobalt, samarium-cobalt, neodyme-iron-boron).

In reference first to FIGS. 1 and 2, FIGS. 1A (top view) and 1B (sectional view along line I-I of FIG. 1A) show the base 20 of the electrical connector.

The base 20 comprises an upper layer 21 (with thickness $e_E$) having an electrical and magnetic function, and a lower layer 22 (with thickness $E_E$) having a mechanical function.

The base 20 comprises a plurality of cylindrical holes 23 (with diameter $D_E$) traversing the upper layer 21 and the lower layer 22.

The holes 23 here form of periodic network (with period $P_E$). The upper layer 21 is for example a sheet of magnetic stainless steel; it may be a flexible sheet.

The lower layer 22 is for example a sheet of polymer or textile material; it may be a flexible layer.

Advantageously, the thickness $e_E$ of the upper layer 21 is comprised between 0.001 mm and 0.5 mm, and preferably, between 0.01 mm and 0.2 mm. For example, the upper layer 21 is a flexible sheet of AISI 420 magnetic stainless steel, with thickness $e_E$=0.075 mm.

Advantageously, the thickness $E_E$ of the lower layer 22 is comprised between 0.1 mm and 5 mm, preferably between 0.5 mm and 2 mm. For example, the lower layer 22 is a flexible layer, made from silicone elastomer or polyurethane foam, with thickness $E_E$=1 mm.

The diameter $D_E$ of the holes 23 is advantageously comprised between 0.1 mm and 10 mm, and preferably between 0.5 mm and 5 mm. The period $P_E$ of the network of holes 23 is advantageously comprised between $1.5 \times D_E$ and $10 \times D_E$, and preferably between $1.5 \times D_E$ and $5 \times D_E$.

FIGS. 2A (top view) and 2B (sectional view along line II-II in FIG. 2A) show a first example plug 100 of the electrical connector.

This plug is secured to an electrical conductor, for example a wire or a power cable (not shown in the FIGURES).

Examples of such electrical conductors will be described in reference to FIG. 20.

The plug 100 comprises a cylindrical part 101, with diameter $D_F$ and thickness $E_F$, having an electrical and magnetic function, and a cylindrical part 102, with diameter $d_F$ and thickness $e_F$, forming a protuberance.

The two cylindrical parts 101 and 102 are centered around the same axis.

The part 101 is for example a part made from aluminum-nickel-cobalt, or samarium-cobalt, or neodyme-iron-boron, which are magnetized electrically conductive materials.

The protuberance 102 is for example a metal part.

Figure 2C:
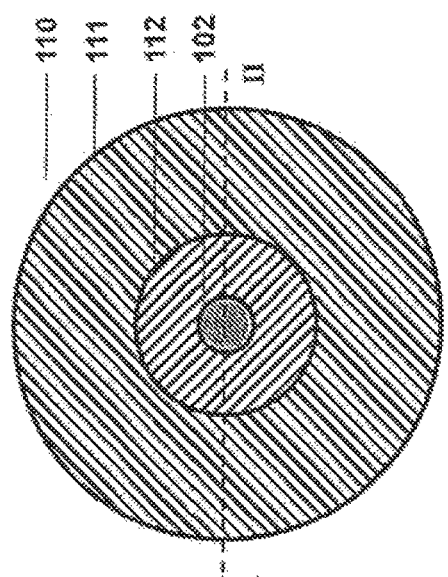

FIGS. 2C (top view) and 2D (sectional view along line II-II in FIG. 2C) show a second example plug 110.

In place of the part 101, the plug 110 comprises an annular part 111 having a magnetic function and a cylindrical part 112 having an electrical function, placed in the central recess of the part 111. The three parts 111, 112 and 102 are centered around a same axis.

The part 111 is for example a part made from ferrite, or aluminum-nickel-cobalt, or samarium-cobalt, or neodyme-iron-boron, which are magnetized materials. The part 112 is for example a metal part.

Figure 2E:
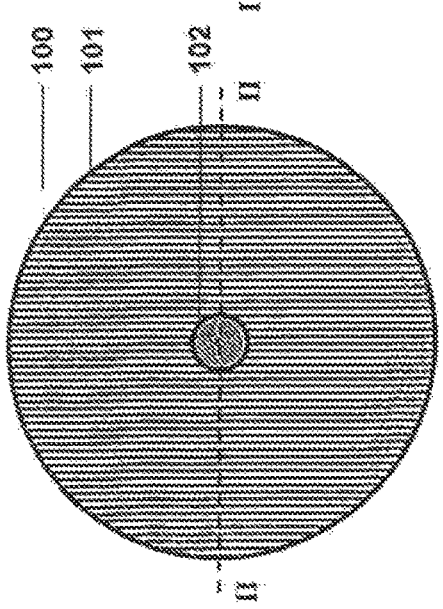

FIGS. 2E (top view) and 2F (sectional view along line II-II in FIG. 2E) show a plug 120 that is an alternative of the plug 110.

In the plug 120, the annular part 121 having a magnetic function is slightly withdrawn (advantageously by several millimeters) from the cylindrical part 122 having an electrical function.

The outer diameter $D_F$ of the part 101, 111 or 121 is greater than the $D_E$. The diameter $d_F$ of the protuberance 102 is smaller than $D_E$.

The thickness $e_F$ of the protuberance 102 is advantageously slightly smaller than the sum $e_E+E_E$. For example, $e_E=0.075$ mm, $E_E=1$ mm, $D_E=1$ mm, $P_E=4$ mm, $D_F=6$ mm, $E_F=1$ mm, $d_F=0.8$ mm, and $e_F=0.8$ mm.

Figure 2B:
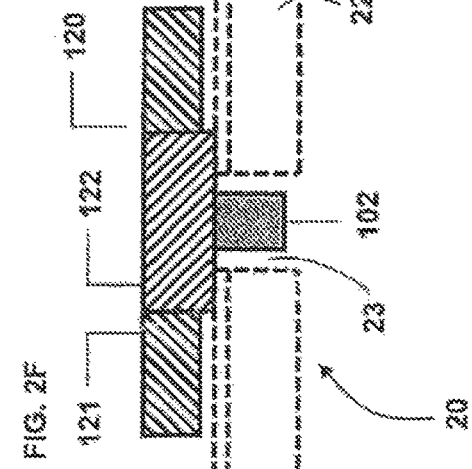

FIG. 2B also shows the plug 101 once connected to the base 20, which is partially shown in dotted lines.

One of the holes 23 accommodates the protuberance 102, which prevents accidental disconnection due to lateral forces, i.e., forces in the plane of the base 20. The upper layer 21 establishes electrical contact with the part 101. The upper layer 21 and the part 101 exert an attractive magnetic force on one another.

The intensity of the magnetic force between the upper layer 21 and the part 101 in particular depends on the nature and dimensions of the upper layer 21 and the part 101.

According to the physical laws of magnetism, the intensity of the magnetic force also depends on the architecture of the plug 100 containing the part 101. For example, by placing the magnetized part 101 in a cup-shaped ferromagnetic part (not shown in FIG. 2B), it is possible to concentrate the magnetic flow on the free edges of the magnetized part 101, which increases the magnetic force. Advantageously, the intensity of the magnetic force is comprised between 100 g and 1000 g. Such an intensity range is achievable with the materials and dimensions previously mentioned, in particular if the part 101 is made from neodyme-iron-boron.

Figure 2D:
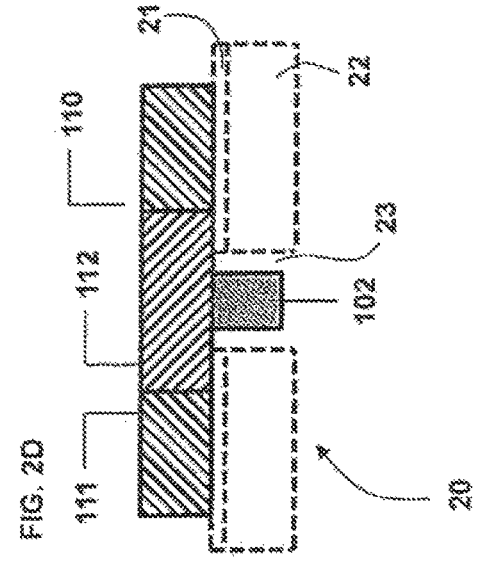

FIG. 2D also shows the plug 110 once connected to the base 20.

The upper layer 21 establishes electrical contact with the part 112. The upper layer 21 and the part 111 exert an attractive magnetic force on one another.

Figure 2F:
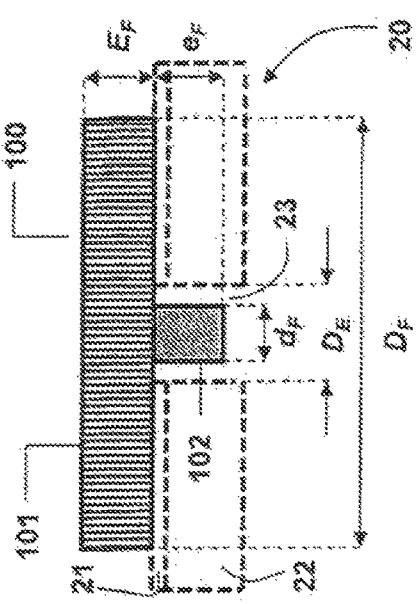

FIG. 2F also shows the plug 120 once connected to the base 20.

The upper layer 21 establishes electrical contact with the part 122. The upper layer 21 and the part 121 exert an attractive magnetic force on one another.

Given that the part 121 is slightly withdrawn from the part 122, the pressure exerted by the part 122 on the upper layer 21 is increased, and therefore the electrical contact between the upper layer 21 and the part 122 is improved. In other words, the electrical resistance of the contact is decreased.

Figure 3A:
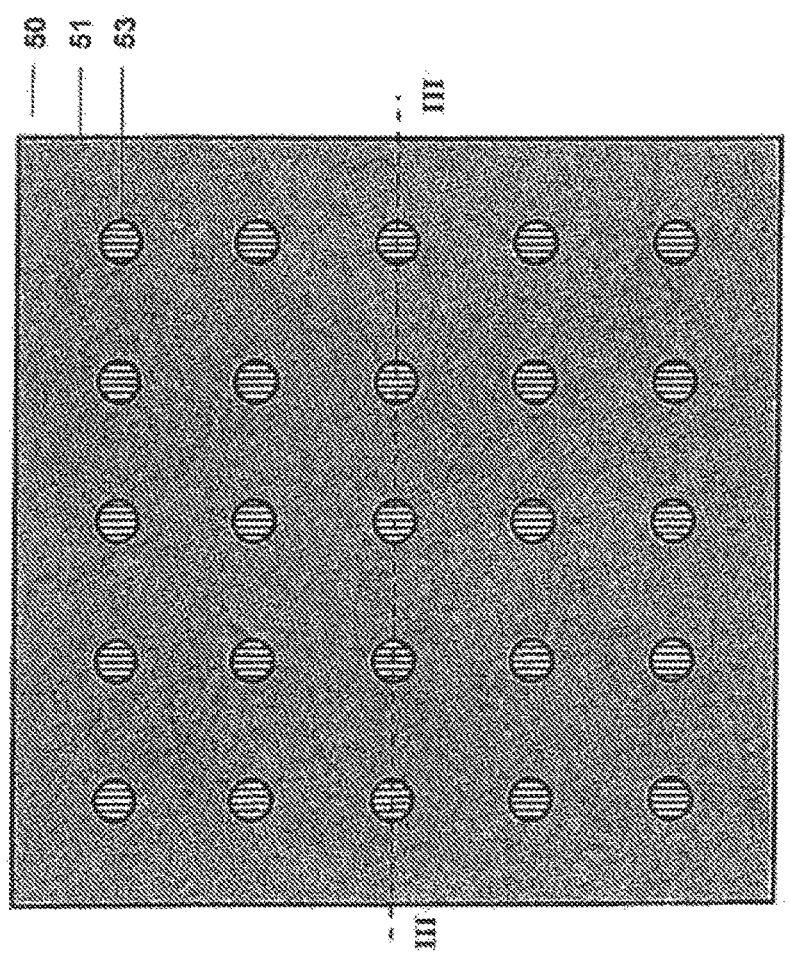

In reference now to FIGS. 3 and 4, FIGS. 3A (top view) and 3B (sectional view along line in FIG. 3A) show the base 50 of the electrical connector.

The base 50 comprises an upper layer 51 having a mechanical function, and a lower layer 52 having an electrical and magnetic function.

The base 50 comprises a plurality of cylindrical holes 53 traversing only the upper layer 51. The holes 53 here form a periodic network.

The upper layer 51 is for example a flexible layer made from polymer or textile material or made from silicone elastomer or polyurethane foam, the thickness of which is 1 mm.

The lower layer 52 is for example a flexible sheet of magnetic stainless steel, for example AISI 420 magnetic stainless steel, the thickness of which is 0.075 mm.

Relative to the first form illustrated in FIG. 1, one advantage of the second form lies in the fact that the layer of the base having an electrical function is not the upper layer of the base. This provides a gain in terms of the safety and reliability of the device.

Indeed, the user cannot easily access the parts intended to be powered on (such as the layer having an electrical function), which limits the electrical risks (for the user) and the risks of malfunction (for the device).

Figure 4A:
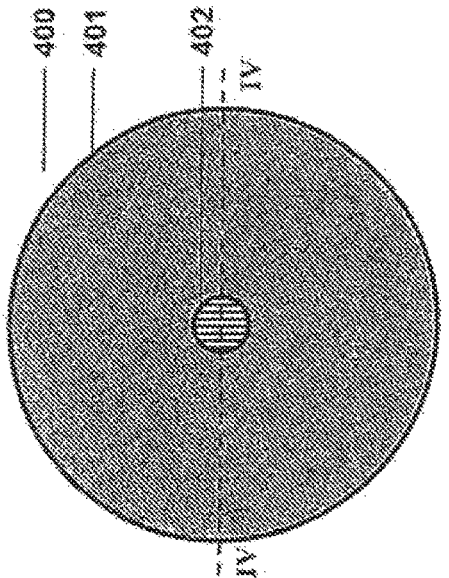

FIGS. 4A (top view) and 4B (sectional view along line IV-IV in FIG. 4A) show a first example of the plug 400 of the electrical connector.

The plug 400 comprises a cylindrical part 401. The plug 400 comprises another cylindrical part 402 forming a protuberance and performing an electrical and magnetic function.

The two cylindrical parts 401 and 402 are centered around a same axis.

The part 401 is for example a metal part.

The protuberance 402 is for example a part made from aluminum-nickel-cobalt, or samarium-cobalt, or neodyme-iron-boron, which are magnetized electrically conductive materials.

Figure 4C:
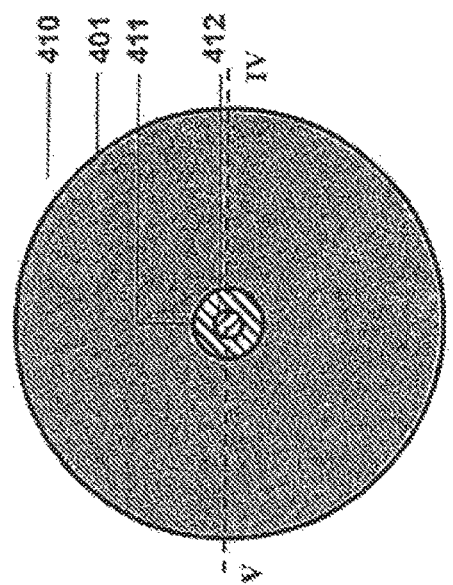

FIGS. 4C (top view) and 4D (sectional view along line IV-IV in FIG. 4C) show a second example of a plug 410.

In place of the protuberance 402, the plug 410 comprises a protuberance 413 formed from an annular part 411 having a magnetic function and a central cylindrical part 412 having an electrical function.

The three parts 401, 411 and 412 are centered around a same axis.

The part 411 is a part for example made from ferrite, or aluminum-nickel-cobalt, or samarium-cobalt, or neodyme-iron-boron, which are magnetized materials. The part 412 is for example a part made from metal.

Figure 4E:
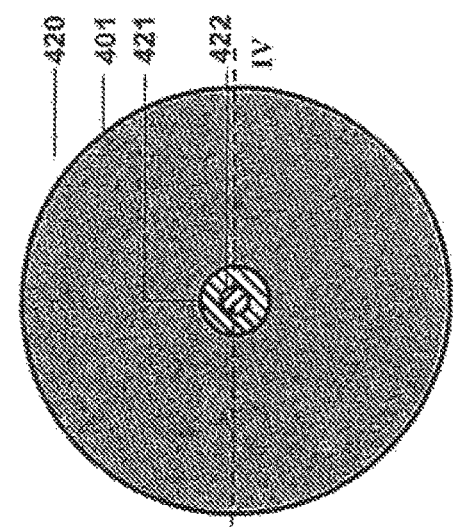

FIGS. 4E (top view) and 4F (sectional view along line Iv-Iv in FIG. 4E) show a plug 420 that is an alternative of the plug 410.

In the protuberance 423 of the plug 420, the annular part 421 having a magnetic function is slightly withdrawn (advantageously by several millimeters) from the central cylindrical part 422 having an electrical function.

Figure 4B:
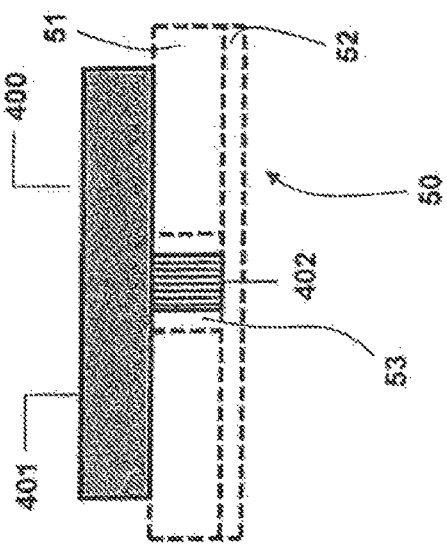

FIG. 4B also shows the plug 400 once connected to the base 50.

One of the holes 53 receives the protuberance 402, which prevents accidental disconnection due to lateral forces, i.e., forces in the plane of the base 50.

The lower layer 52 establishes electrical contact with the protuberance 402.

The lower layer 52 and the protuberance 402 exert an attractive magnetic force on one another.

Advantageously, the height of the protuberance 402 is equal to or slightly greater than the thickness of the layer 51.

However, the height of the protuberance 402 can be slightly smaller than the thickness of the layer 51. In this case, the compressibility of the layer 51 or the flexibility of the layer 52 make it possible to adapt to the situation to produce electrical contact.

In order to improve the electrical contact between the lower layer 52 and the protuberance 402, and to avoid dirtying of these parts that may lead to poor electrical contact, the lower layer 52 and the protuberance 402 can have shapes different from those shown in FIG. 4B.

In particular, the end of the protuberance 402, i.e., the part coming into contact with the lower layer 52, is not necessarily planar, but may have a rounded or pointed shape. In this case, the exposed zones of the lower layer 52, i.e., the zones on which the holes 53 emerge, are not necessarily planar, but may be in the form of a cavity making it possible to receive the rounded or pointed end of the protuberance 402.

Another method for improving the electrical contact between the protuberance 402 and the base 50 consists of metallizing the inner walls of the holes 53. In this case, the protuberance 402 can establish electrical contact via its end or via its flanks.

Figure 4D:
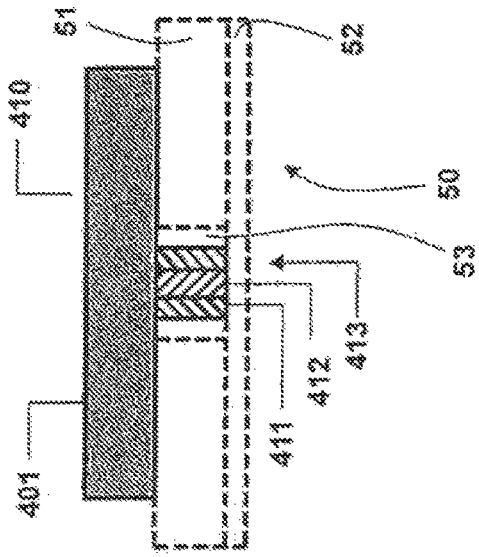

FIG. 4D also shows the plug 410 once connected to the base 50.

The lower layer 52 establishes electrical contact with the part 412.

The lower layer 52 and the part 411 exert an attractive magnetic force on one another.

Figure 4F:
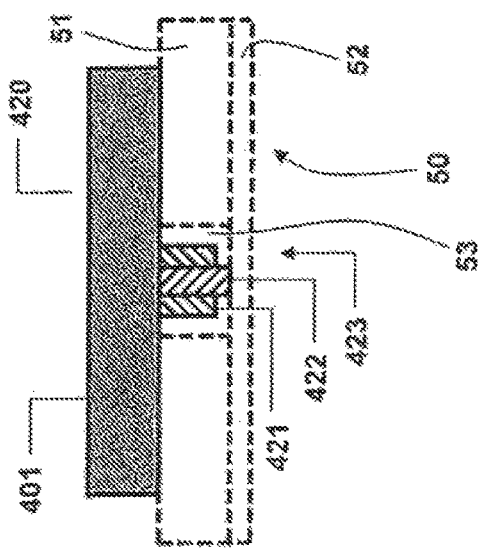

FIG. 4F also shows the plug 420 once connected to the base 50.

The lower layer 52 establishes electrical contact with the part 422.

The lower layer 52 and the part 421 exert an attractive magnetic force on one another.

Given that the part 421 is slightly withdrawn from the part 422, the pressure exerted by the part 422 on the lower layer 52 is increased, and therefore the electrical contact between the lower layer 52 and the part 422 is improved. In other words, the electrical resistance of the contact is decreased.

In reference to FIGS. 5 and 6, FIGS. 5A (top view) and 5B (sectional view along line V-V in FIG. 5A) show the base 80 of the electrical connector.

The base 80 comprises an upper layer 81 having a magnetic function, an intermediate layer 84 having a mechanical function, and a lower layer 82 having an electrical function.

The base 80 comprises a plurality of cylindrical holes 83 traversing only the upper layer 81 and the intermediate layer 84. The holes 83 here form of periodic network.

The upper layer 81 is for example a flexible sheet of magnetic stainless steel, in particular an AISI 420 magnetic stainless steel, with a thickness of 0.075 mm.

The intermediate layer 84 is for example a flexible layer made from polymer or textile material, or a silicone elastomer or polyurethane foam, the thickness of which is 1 mm.

The lower layer 82 is for example a metal-polymer bilayer (the metal layer being above the polymer layer) or a copper-polyamide bilayer (with a copper layer having a thickness of 0.035 mm and a polyamide layer with a thickness of 0.045 mm).

Relative to the first form illustrated in FIG. 1, one advantage of this third form lies in the fact that the layer of the base having an electrical function is not the upper layer of the base, which provides a gain in terms of the safety and reliability of the device.

FIGS. 6A (top view) and 6B (sectional view along line VI-VI in FIG. 6A) show the plug 700 of the electrical connector.

The plug 700 comprises an annular part 701 forming its base, having a magnetic function, and a central cylindrical part 702 forming a protuberance 702a, protruding relative to the annular part 701, and having an electrical function.

The two parts 701 and 702 are centered around a same axis.

The part 701 is for example a ferrite part, or aluminum-nickel-cobalt or samarium-cobalt or neodyme-iron-boron, which are magnetized materials.

The protuberance 702 is for example a metal part.

FIG. 5B also shows the plug 700 once connected to the base 80.

One of the holes 83 accommodates the protuberance 702a, which prevents an accidental disconnection due to lateral forces, i.e., forces in the plane of the base 80.

The lower layer 82 establishes electrical contact with the protuberance 702. The upper layer 81 and the part 701 exert an attractive magnetic force on one another.

The height of the protuberance 702a is equal to or slightly larger than the sum of the thicknesses of the layers 81 and 84.

In order to improve the electrical contact between the lower layer 82 and the protuberance 702a, and prevent dirtying of these parts that may lead to poor electrical contact, the lower layer 82 and the protuberance 702a may have shapes different from those shown in FIGS. 5 and 6.

In particular, the end of the protuberance 702a, i.e., the part coming into contact with the lower layer 82, is not necessarily planar, but may have a rounded or pointed shape.

In this case, the exposed zones of the lower layer 82, i.e., the zones on which the holes 83 emerge, are not necessarily planar, but can be in the form of a cavity making it possible to receive the rounded or pointed end of the protuberance 702.

Another method for improving the electrical contact between the protuberance 702 and the base 80 consists of analyzing the inner walls of the holes 83. In this case, the protuberance 702 can establish electrical contact via its end or via its flanks.

In all of the forms illustrated in FIGS. 1 to 6, the holes of the base are cylindrical, and the plug has a symmetry of revolution around an axis perpendicular to the plane of the base.

This is advantageous, since in this way, the electrical connection between the plug and the base can be established for any orientation of the plug. Of course, the plane of the plug should be parallel to the plane of the base, which is in particular ensured by the magnetic forces.

However, the disclosure is not limited to this form.

Furthermore, in all of the forms illustrated in FIGS. 1 to 6, the base and the plug include a part performing a magnetic function.

However, even in the absence of parts performing a magnetic function, the connectors described in reference to these FIGURES make it possible to produce an electrical connection with no visual inspection.

FIGS. 7 to 17 show alternative embodiments of the connector illustrated in FIGS. 1 to 6.

Thus, FIGS. 7 and 8 illustrate a first alternative.

FIGS. 7A (top view) and 7B (sectional view along line VII-VII in FIG. 7A) show the plug 1000 of the electrical connector.

Relative to the plug 100 illustrated in FIG. 2, the plug 1000 additionally comprises an annular part 1001 forming a protuberance.

The three parts 101, 102 and 1001 are centered around a same axis.

The plug 1000 retains a symmetry of revolution around an axis.

Figure 8A:
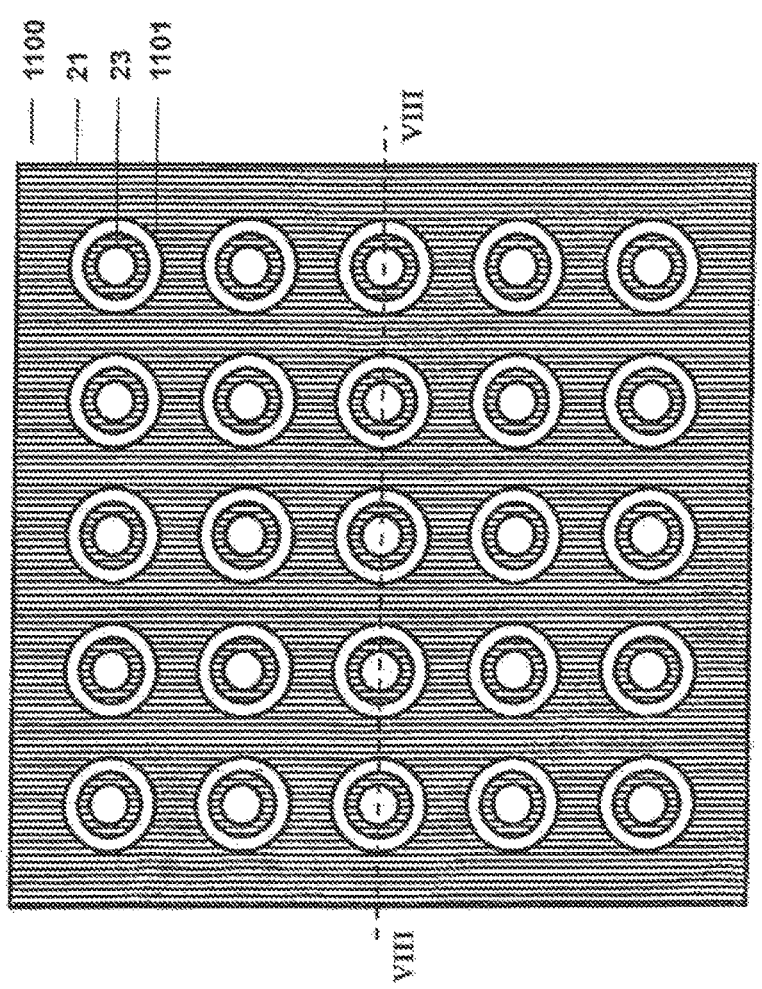

FIGS. 8A (top view) and 8B (sectional view along line VIII-VIII in FIG. 8A) show the base 1100 of the electrical connector, modified to adapt to the plug illustrated in FIG.

7. Thus, relative to the base 20 illustrated in FIG. 1, the base 1100 additionally comprises annular holes 1101.

Each hole 23 is surrounded by an annular hole 1101, the two holes being centered around a same axis. The assembly formed by a cylindrical hole 23 and an annular hole 1101 therefore has a symmetry of revolution around the same central axis.

Figure 8B:
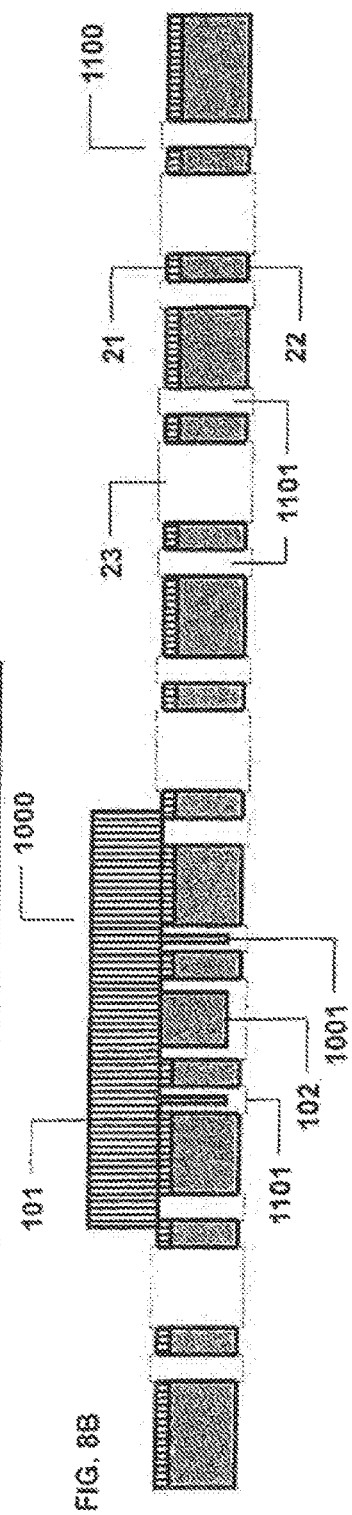

FIG. 8B shows the plug 1000 once connected to the base 1100.

One of the cylindrical holes 23 receives the protuberance 102, while the corresponding annular hole 1101 receives the protuberance 1001.

Relative to the case described in FIG. 2B, the mechanical strength of the connection with respect to the lateral forces is improved, since an additional protuberance (the protuberance 1001) is present.

Advantageously, the diameter of the protuberance 102 is such that the protuberance 102 cannot be introduced into an annular hole 1101.

This first alternative is described in relation to FIGS. 1 and 2, but it also applies to the connector described in relation to FIGS. 3, 4 and 5, 6.

FIGS. 9 and 10 illustrate a second alternative embodiment of the connector.

FIG. 9 shows the plug 1300 of the electrical connector.

Unlike the protuberance 102 of the plug 100 illustrated in FIG. 2B, the protuberance 1301 of the plug 1300 has a flared shape close to its base. In other words, the diameter of the protuberance decreases moving away from the base 101 of the plug. The plug 1300 retains a symmetry of revolution around an axis.

FIG. 10 shows the base 1302 of the electrical connector. Unlike the holes 23 of the base 20 illustrated in FIG. 1, the holes 1303 of the base 1302 have a flared shape close to the layer 21 of the base. In other words, the holes widen near the layer 21. Each hole 1303 retains a symmetry of revolution around an axis.

FIG. 10 also shows the plug 1300 once connected to the base 1302. The flared shape of the protuberance 1301 and the holes 1303 facilitates the connection, by guiding the insertion of the protuberance 1301 into a hole 1303.

This second alternative is described in relation to FIGS. 1 and 2, but it also applies to the connector described in relation to FIGS. 3, 4 and 5, 6.

FIGS. 11 and 12 illustrate a third alternative embodiment of the connector.

FIG. 11 illustrates the plug 1500 of the electrical connector.

Unlike the protuberance 402 of the plug 400 illustrated in FIG. 4B, the protuberance 1504 of the plug 1500 makes it possible to transmit not a single electrical signal, but two electrical signals.

Indeed, the protuberance of the plug 1500 is made up of a central cylindrical part 1501 having an electrical and magnetic function, an annular part 1502 having an electrically insulating function, and an annular part 1503 having an electrical and magnetic function. The parts 1501 and 1503, electrically insulated by the part 1502, can each transmit a different electrical signal.

The four parts 401, 1501, 1502 and 1503 are centered around a same axis. The plug 1500 thus retains a symmetry of revolution around a same axis.

Figure 12A:
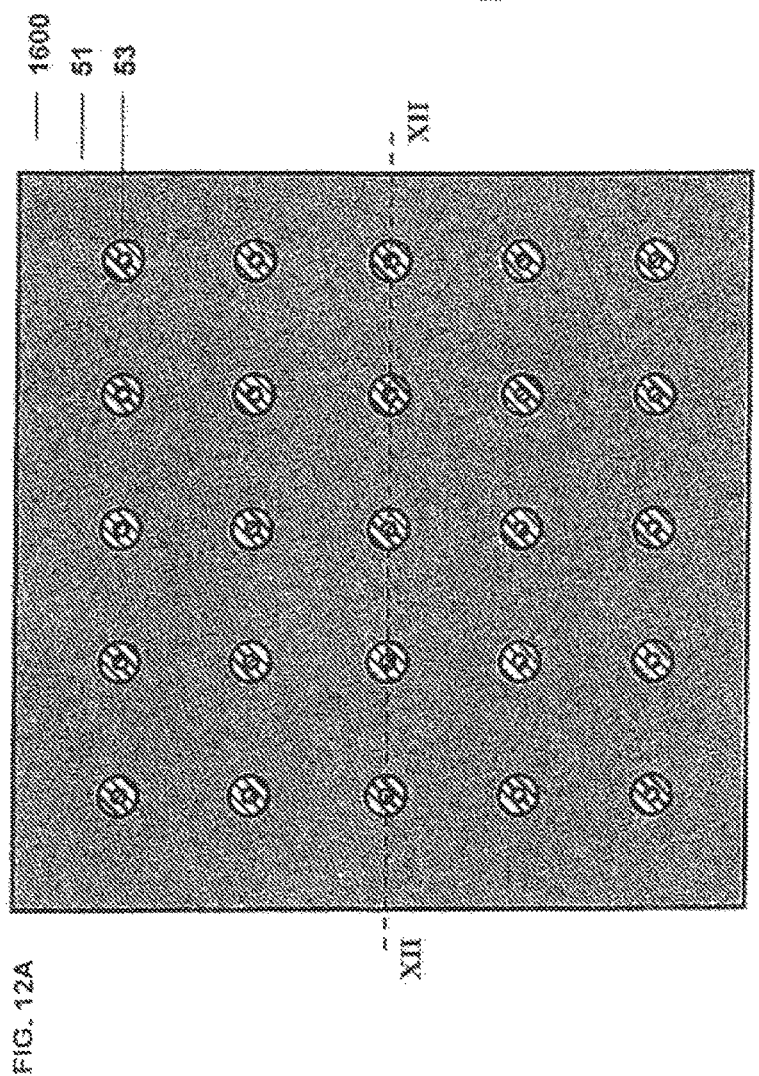

FIGS. 12A (top view) and 12B (sectional view along line XII-XII in FIG. 12A) show the base 1600 of the electrical connector, modified to adapt to the plug illustrated in FIG. 11.

Unlike the lower layer 52 of the base 50 illustrated in FIG. 3, the lower layer of the base 1600 makes it possible to transmit not a single electrical signal, but two electrical signals.

Indeed, the lower layer of the base 1600 is made up of a layer 1601 playing an electrical and magnetic role, a layer 1602 having an electrically insulating function, and a layer 1603 having an electrical and magnetic function. The layers 1601 and 1603, electrically insulated by the layer 1602, can each transmit a different electrical signal.

Figure 12B:
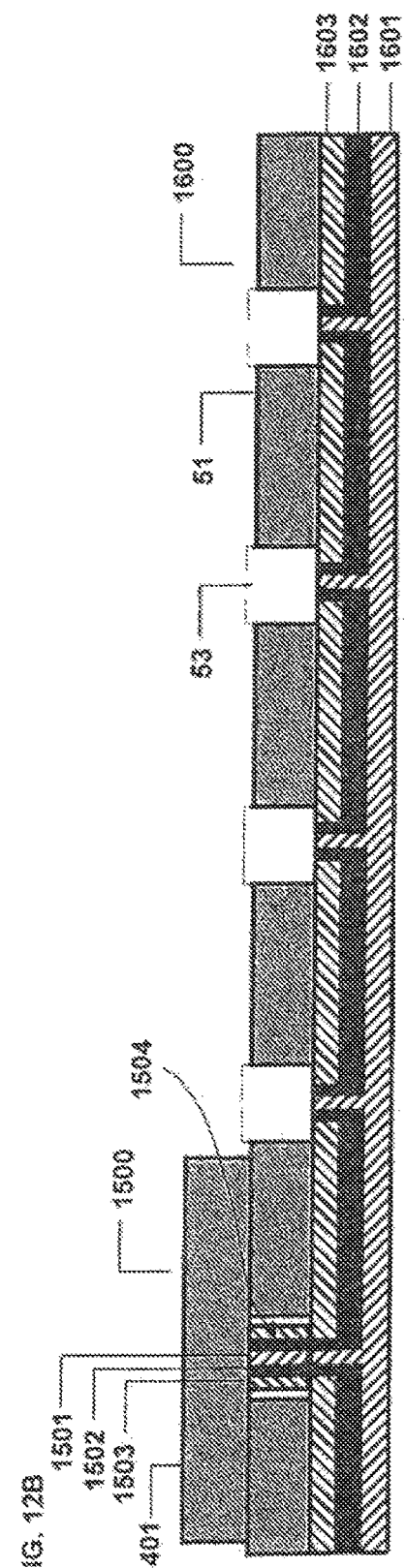

FIG. 12B also shows the plug 1500, once connected to the base 1600.

The layer 1601 establishes electrical contact with the part 1501. Furthermore, the layer 1601 and the part 1501 exert an attractive magnetic force on one another.

The layer 1603 establishes electrical contact with the part 1503. Furthermore, the layer 1603 and the part 1503 exert an attractive magnetic force on one another.

This third alternative is described in relation to FIGS. 3 and 4, but it also applies to the connector described in reference to FIGS. 5 and 6.

Figure 13:
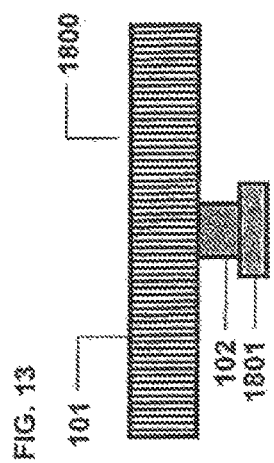
FIG. 13 is a sectional view showing a fourth alternative embodiment of a male plug adapted to the female bases described in reference to FIGS. 1, 3 and 5.

FIGS. 13 and 14 illustrate a fourth alternative embodiment of the connector according to the disclosure.

FIG. 13 shows the plug 1800 of the electrical connector.

Relative to the plug 100 illustrated in FIG. 2B, the plug 1800 has a shape widening as it moves away from the base. More particularly, the plug 1800 illustrated in FIG. 3 comprises a cylindrical part 1801 fastened to the end of the protuberance 102, the diameter of the cylindrical part 1801 being larger than that of the cylindrical part 102. The three parts 101, 102 and 1801 are centered around a same axis. The plug 1800 therefore retains a symmetry of revolution around a same axis.

FIG. 14 shows the base 1802 of the electrical connector, which is of the type illustrated in FIG. 1. It shows that the upper 21 and lower 22 layers of the base 1802 are modified to adapt to the plug illustrated in FIG. 13.

The holes 1803 traversing the upper layer 21 have a different shape from the holes 1804 traversing the lower layer 22. Thus, the holes 1803 are formed by a large cylinder and a small cylinder, while the holes 1804 are simply cylindrical. The holes 1803 and 1804 are aligned, as shown in FIG. 14 (the dotted lines of this FIGURE indicate the position of the holes 1804 relative to the holes 1803).

The diameter of the part 102 is smaller than the diameter of the small cylinder of the holes 1803, and therefore smaller than the diameter of the large cylinder of the holes 1803. The diameter of the part 1801 is larger than the diameter of the small cylinder of the holes 1803, but smaller than the diameter of the large cylinder of the holes 1803.

The protuberance of the plug 1800 is inserted in the base 1802, first passing through the large cylinder of the hole 1803, then through the underlying hole 1804. After this insertion, the part 1801 is found in the hole 1804, at the vertical of the large cylinder of the hole 1803. In this so-called "unlocked" position, the protuberance of the plug 1800 prevents accidental disconnection due to lateral forces, but does not oppose any resistance to vertical forces.

From the "unlocked" position, the protuberance of the plug 1800 can be moved laterally to the right such the part 1801 remains of the hole 1804 but is found at the vertical of the small cylinder of the hole 1803. In this so-called "locked" position, the protuberance of the plug 1800 prevents an accidental disconnection due to lateral forces, and moreover opposes resistance to vertical forces. Indeed, the diameter of the part 1801 is larger than the diameter of the small cylinder of the hole 1803.

The electrical connector shown in FIGS. 13 and 14 therefore makes it possible to strengthen the resistance to an accidental disconnection, by placing the plug in a "locked" position.

Other shapes of holes 1803 can be considered to provide a "locked" mode. For example, the holes 1803 can be formed by a large cylinder surrounded by a plurality of small cylinders.

Figure 15E:
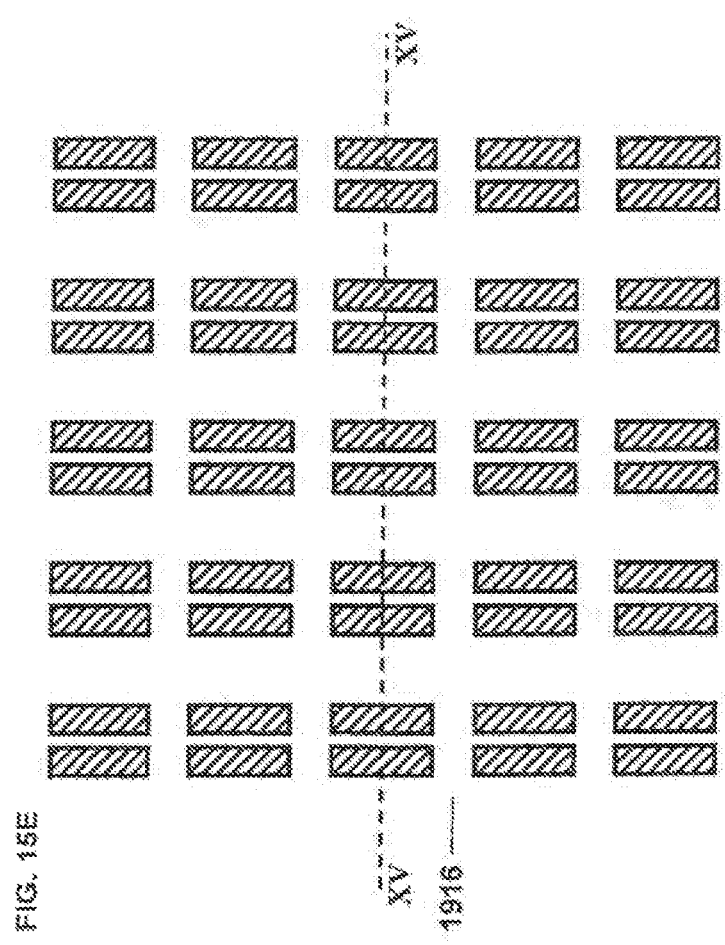
Figure 16:
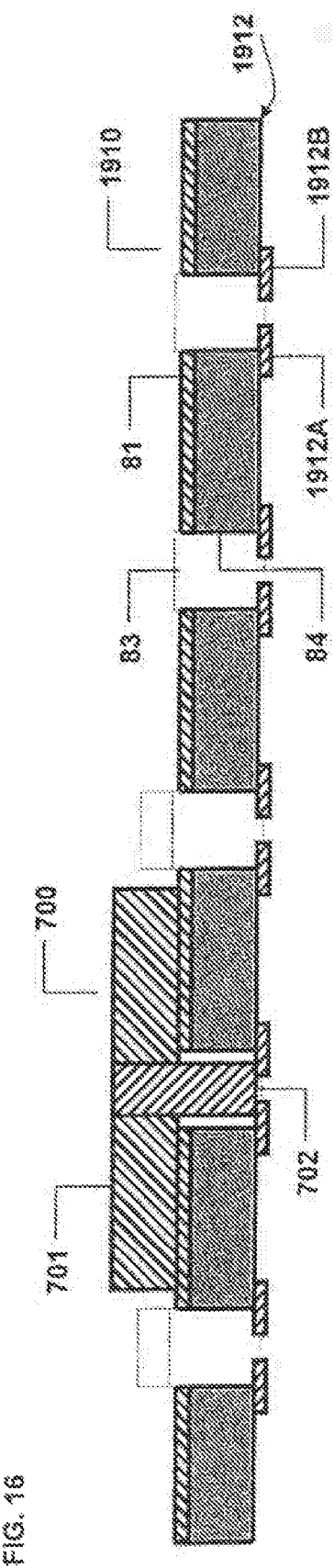
FIG. 16 is a sectional view of a base of the type illustrated in FIG. 15D according to the fifth alternative embodiment, a male plug of the type illustrated in FIG. 6 being connected on this base, FIG. 17 (17A-17B) comprises a top view (FIG. 17A) and a sectional view (FIG. 17B) showing a sixth alternative embodiment of the base illustrated in FIG. 5.

FIGS. 15 and 16 illustrate a fifth alternative embodiment of a connector including a base of the type illustrated in FIGS. 3 and 5, i.e., including a lower layer 52 or 82 not traversed by holes.

Figure 3B:
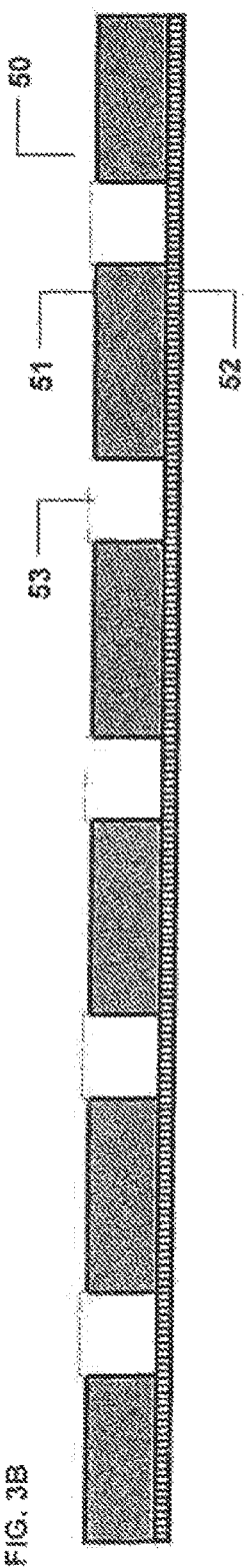

FIG. 15A shows the lower curve 1401 of the base according to the fifth alternative, the sectional view of which along line XIV-XIV of FIG. 15A is similar to that of the base 50 illustrated in FIG. 3B or FIG. 5B. Unlike the lower layer 52 of the base 50 illustrated in FIG. 3, the lower layer 1401 of this base is not a continuous layer, but a layer in grid form: the flexibility of the lower layer is therefore improved. This grid is made up of horizontal strips 1401a and vertical strips 1401b. The holes 53 emerge in solid zones of the grid 1401.

The lower layer of the base can assume other forms, like those illustrated in FIGS. 15B and 15C.

Thus, the lower layer 1402 includes as many vertical strips 1402b as the grid 1401 of FIG. 15A, but only two horizontal strips 1402a.

The lower layer 1403 includes only a single horizontal strip 1403a and as many vertical strips 1403b as the grid 1401.

The interest of the layers 1402 and 1403 is to further increase the mechanical flexibility of the lower layer of the base.

These embodiments are possible as long as the material forming the lower layer has a high enough electrical conductivity. Indeed, in this case, all of the horizontal strips of FIG. 15A are not necessarily needed to conduct electrical current.

FIG. 15D shows the lower curve 1912 of the base of the electrical connector. Unlike the lower layer 82 of the base 80, illustrated in FIG. 5, the lower layer 1912 of the base illustrated in FIG. 15D is not a continuous layer, but a layer made up of two parts 1912A and 1912B that are separate and not electrically connected.

FIG. 16 is a sectional view of the base along line XVI-XVI in FIG. 15D. It illustrates that the holes 83 of the base emerge over zones comprising both a portion of the part 1912A and a portion of the part 1912B. In the case of the example illustrated in FIG. 15D, the two parts 1912A and 1912B form an interdigitated structure, but other forms and structures can be considered.

FIG. 16 shows the plug 700 once connected to the base 1910. The two parts 1912A and 1912B establish electrical contact with the protuberance 702a. Furthermore, the protuberance 702a makes it possible to connect the part 1912A electrically to the part 1912B.

Thus, the base 1910 performs both a connector and switch function. This is particularly advantageous, as will be explained in the continuation of the description.

Furthermore, the fact that the lower layer 1912 is not a continuous layer may advantageously give the base 1910 greater flexibility.

In the example illustrated in FIG. 15D, the lower layer is made up of two separate parts that are not electrically connected.

It is possible to generalize this concept to the case of a higher number of separate parts that are not electrically connected: this is for example the case of the lower layer 1916, illustrated in FIG. 15E, intended for another base, the sectional view of which along line XV-XV of FIG. 15E is similar to that of the base 1910 illustrated in FIG. 16.

This base can make it possible to detect the hole 83 in which the protuberance 702a is connected. This may for example be obtained by electronic impedance measuring means.

This is advantageous in particular for safety reasons. Control electronics can then act such that the electrical power is oriented only toward the hole 83 in which the protuberance 702a is connected, and not in the other holes of the base 1915.

Figure 17A:
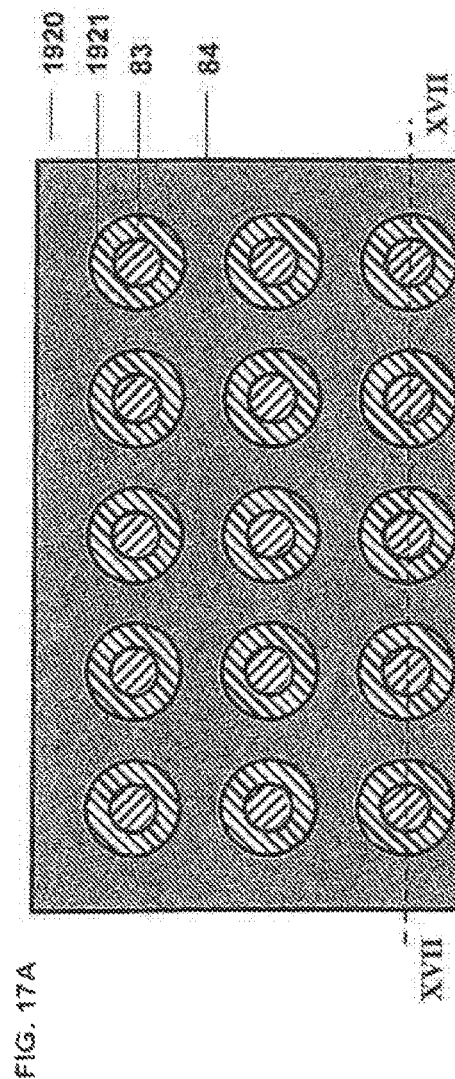
Figure 17B:
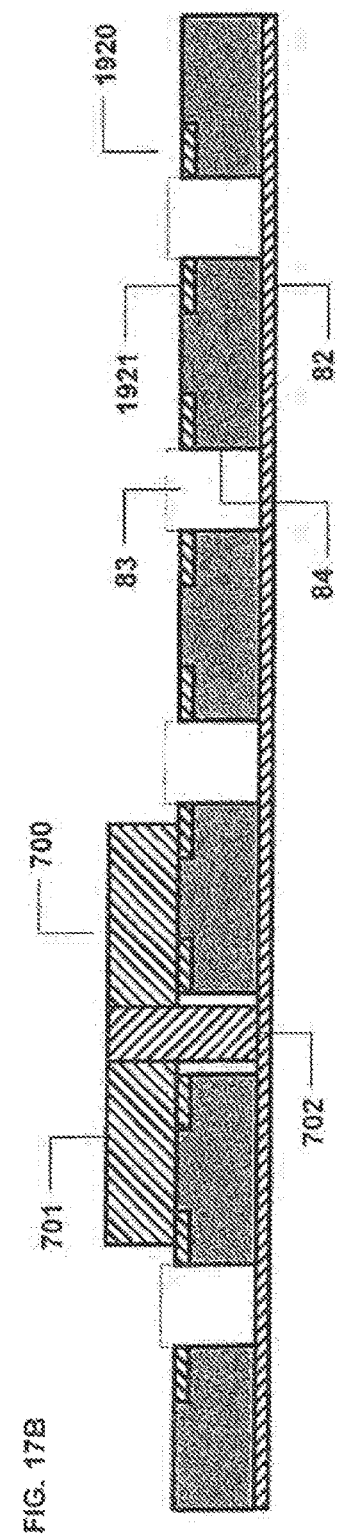

FIG. 17A and FIG. 17B (sectional view along line XVII-XVII of FIG. 17A) show a sixth alternative embodiment of the base illustrated in FIG. 5.

Unlike the upper layer 81 of the base 80, the upper layer 1921 of the base 1920 is not a continuous layer. The flexibility of the upper layer is therefore improved.

In the case of the example illustrated in FIG. 17, the upper layer 1921 is formed by a plurality of rings not mechanically connected, but other shapes and structures can be considered (for example, a plurality of rings connected to one another by strips).

FIG. 17B also shows the plug 700 once connected to the base 1920.

In an alternative embodiment not illustrated in the FIGURES, the protuberances of the plugs perform an elastic function. They may thus be spring-mounted ("pogo pins") or mounted on an elastomer material acting as a spring. Alternatively, the protuberances of the plugs can be made entirely from an electrically conductive elastomeric material, for example an elastomeric material filled with metal elements. This may allow a better electrical contact to be established.

FIGS. 18 and 19 diagrammatically show how the electrical connector according to the disclosure can be used in electrostimulation devices:
a self-adhesive cutaneous electrode 1900, which comprises a base 1901 according to the third embodiment of the disclosure (FIG. 5B),
a patch 2000 generating impulses, which comprises a base 2001 according to the fifth alternative embodiment (FIG. 16).

Electrical connectors according to other embodiments of the disclosure can also be used in such electrostimulation devices.

FIG. 18 shows that the cutaneous electrode 1900 comprises an electrically conductive substrate 1902, for example a polymer filled with carbon black or metallic elements, or a conductive textile material, and hydrogel layers 1903, intended to establish electrical contact with the user's skin.

The cutaneous electrode 1900 comprises, on its upper face, a base 1901 according to the third embodiment of the disclosure. The base 1901 makes it possible to connect the cutaneous electrode 1900 to an electrical wire comprising a plug.

FIG. 19A shows that the patch 2000 comprises a main part 2002 that in particular contains electronic components and a power source.

It comprises, on its lower face, layers of hydrogel 2003, intended to establish electrical contact with the user's skin, and, on its upper face, a base 2001 according to the fifth alternative of the disclosure.

The base 2001 makes it possible to connect the patch 2000 to an electrical wire comprising a plug.

It may also act as an upper encapsulating layer for the patch 2000.

The base 2001 comprises an upper layer 2004 playing a magnetic role, an intermediate layer 2007 playing a mechanical role, and a lower layer 2005 playing an electrical role.

The lower layer 2005 is made up of two parts 2005A and 2005B, which are separate and not electrically connected. Holes 2006 emerge on zones comprising both a portion of the part 2005A and a portion of the part 2005B.

Figure 19B:
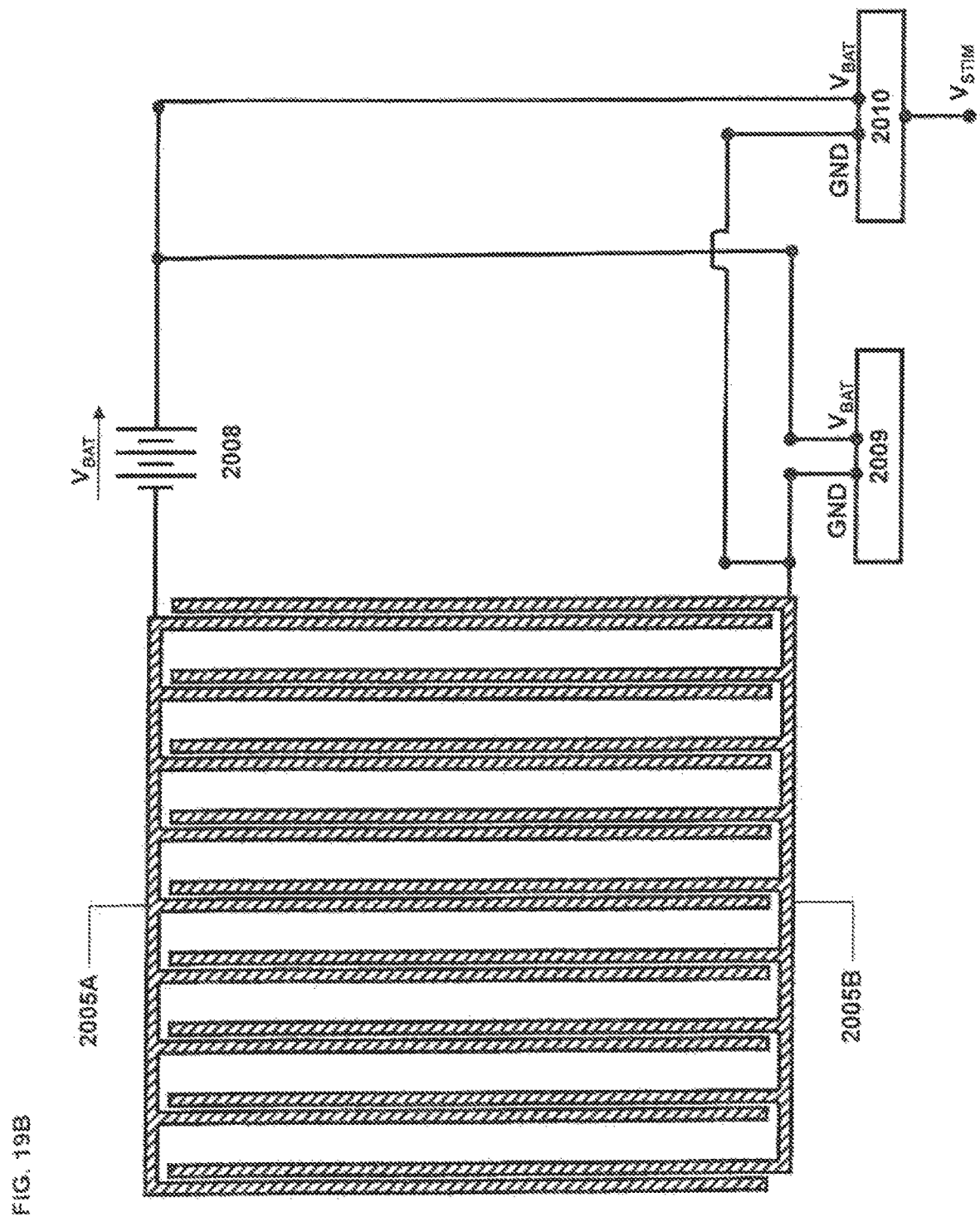

FIG. 19B is an electrical diagram of the patch 2000.

The part 2005A is connected to the negative pole of a power source 2008. The part 2005B is connected to the ground (GND) of the electronic circuits 2009 and 2010. The positive pole of the power source 2008 is connected to the power supplies ($V_{BAT}$) of the electronic circuits 2009 and 2010. The output ($V_{STIM}$) of the electronic circuit 2010 is connected to the hydrogel layers 2003.

The electronic circuit 2010 serves to generate electrostimulation pulses.

The electronic circuit 2009 may have several roles, in particular:

warning the user when the patch 2000 is turned on, for example through a visual or audio signal, a communicating with the user, for example by radio waves, i.e., sending information to the user or receiving information from the user, steering the electronic circuit 2010, i.e., ordering the start or stop of a certain electrostimulation program, characterized in particular by the amplitude, frequency and duration of the pulses.

During the use of the patch 2000, two cases may arise:

No plug is connected to the base 2001 of the patch 2000.

In this case, the switch formed by the two parts 2005A and 2005B is in an open state. Indeed, the two parts 2005A and 2005B are not electrically connected. The electronic circuits 2009 and 2010 are therefore not powered by the power source 2008. In other words, the patch 2000 is turned off and does not consume energy.

A plug is connected to the base 2001 of the patch 2000.

In this case, the switch formed by the two parts 2005A and 2005B is in a closed state. Indeed, the protuberance of the plug, which is inserted in a hole 2006, allows the electrical connection of the part 2005A to the part 2005B. The electronic circuits 2009 and 2010 are therefore powered by the power source 2008. In other words, the patch 2000 is powered on and consumes energy coming from the source 2008.

In this case, as mentioned above, the electronic circuit 2009 can:

warn the user that the patch 2000 is powered on, transmit information to the user or be ready to receive information from the user, steer the electronic circuit 2010.

Thus, in the first case (switch open, patch off), no electrostimulation current circulates in the user's body.

However, in the second case (switch closed, patch powered on), an electrostimulation current does not necessarily circulate in the user's body. Indeed, in order for an electrostimulation current to circulate in the user's body, it is necessary on the one hand for the electrical electrostimulation path to be established, as described later, and on the other hand for the electronic circuit 2009 to authorize the electronic circuit 2010 to start an electrostimulation program.

The advantage of the base 2001 according to the fifth alternative of the disclosure is to perform both a connector and switch function. This makes it possible not to have to integrate a conventional switch into the patch 2000. This is interesting in particular if one wishes for the patch 2000 to remain a thin and flexible object.

FIG. 20A shows a user (seen from behind) wearing the self-adhesive cutaneous electrode 1900 and the patch 2000 on the lower back.

The self-adhesive cutaneous electrode 1900 is connected to the user's skin via the hydrogel layers 1903.

The output ($V_{STIM}$) of the electronic circuit 2010 of the patch 2000 is connected to the user's skin via the hydrogel layers 2003.

FIG. 20A shows that the self-adhesive cutaneous electrode 1900 and patch 2000 are interconnected via an elastic band 2100.

This band 2100 is illustrated in top view in FIG. 20B.

It comprises an electrically conductive track 2103, interconnecting two plugs 2101 and 2102, which are intended to be connected to the bases 1901 and 2001.

The track 2103 is for example a metal/polymer bilayer, fastened on the elastic band 2100. The track 2103 can have a serpentine shape, as for example described in FIG. 3 of the document [R. Carta et al., Design and implementation of advanced systems in a flexible-stretchable technology for biomedical applications, Sensors and Actuators A 156 (2009) 79-87]. In this way, the elastic band 2100 can be stretched without risk of damaging the track 2103.

The plug 2101 on the elastic band 2100 is connected to the base 1901 of the cutaneous electrode 1900. The plug 2102 on the elastic band 2100 is connected to the base 2001 of the patch 2000.

Thus, the negative pole of the energy source 2008 is connected to the user's skin via the hydrogel layers 1903. In this way, an electrical electrostimulation path is established: an electrical current can circulate in the user's body between the hydrogel layers 2003 (which are at the electrical potential $V_{STIM}$) and the hydrogel layers 1903 (which are at the electrical potential of the negative pole of the power source 2008).

The advantages of electrical connector according to the disclosure used in the cutaneous electrode 1900 and the patch 2000 are as follows:

the bases 1901 and 2001 can be thin or even flexible, which is comfortable for the user;

the connection between the cutaneous electrode 1900 and the patch 2000, via the bases 1901 and 2001 and the plugs 2101 and 2102, can be done quickly without exerting pressure on the user's skin and without visual inspection;

the base 1901, 2001, respectively, has a large number of potential connection zones (the holes of the base), these connection zones covering a large portion of the upper surface of the cutaneous electrode 1900 (of the patch 2000, respectively). Thus, for a given length of elastic band 2100, the user is offered great freedom over the distance separating the cutaneous electrode 1900 from the patch 2000. Furthermore, the user can easily connect the elastic band 2100 such that it is not to stretched (in which case the risk of accidental disconnection would be increased, and the elastic band 2100 would be a source of bother since it would compress the user's body), or too slack (in this case, the elastic band 2100 would be a source of bother because it would "dangle").

The elastic band 2100 can comprise a first tongue allowing the user to disconnect the plug 2101 from the base 1901 easily, and a second tongue allowing the user to disconnect the plug 2102 from the base 2001 easily.

Lastly, the elastic band 2100 can be integrated into a piece of clothing.

FIGS. 21 to 26 illustrate several forms of a connector according to the disclosure including a male base and a female plug including a cavity.

The base comprises a stack of layers, advantageously thin or even flexible, and a plurality of protuberances.

Thus, FIGS. 21 and 22 illustrate a first embodiment of such a connector, in which the base comprises:
a plurality of protuberances,
an intermediate layer having an electrical and magnetic function, on which the protuberances are made,
a lower layer having a mechanical function.

One alternative of this first form consists of the intermediate layer being eliminated, the lower layer also performing an electrical function and a potential magnetic function.

Figure 24A:
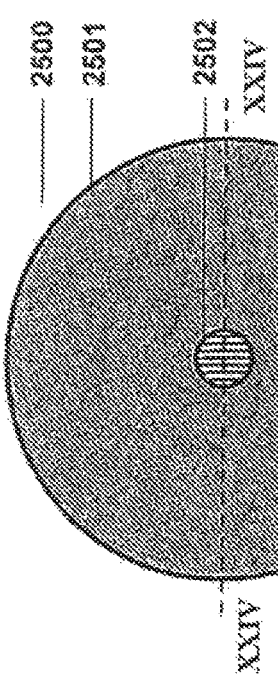
Figure 24B:
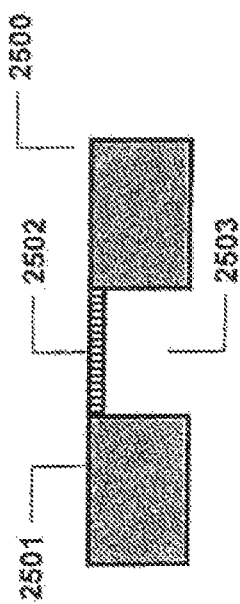

FIGS. 23 and 24 illustrate a second form of such a connector, in which the base comprises:
a plurality of protuberances having an electrical and magnetic function, a lower layer having a mechanical function, on which the protuberances are formed.

Figure 26A:
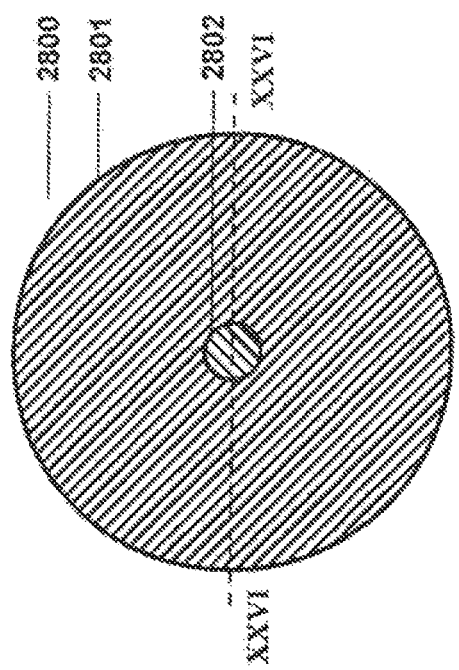
Figure 26B:
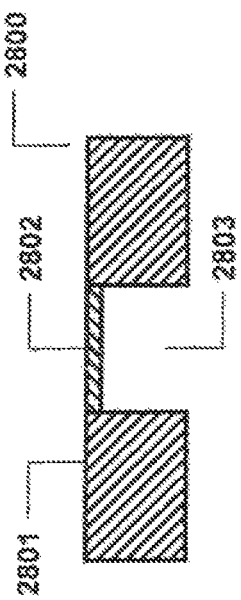

FIGS. 25 and 26 illustrate a third embodiment of such a connector, in which the base comprises:
a plurality of protuberances having a magnetic function,
an intermediate layer having an electrical function, on which the protuberances are formed,
a lower layer having a mechanical function.

One alternative of this third form (not illustrated in the FIGURES) consists of the protuberances performing an electrical function and the intermediate layer performing a magnetic function.

In each of these forms:

The base comprises either protuberances having an electrical function, or a layer having an electrical function. The elements of the base having an electrical function (protuberance or layer) are intended to establish electrical contact with the part of the plug having an electrical function.

The elements of the base having an electrical function are formed from an electrically conductive material.

If the base comprises a layer having an electrical function, this layer is preferably thin, or even flexible.

The base comprises either protuberances having a magnetic function, or a layer having a magnetic function. The elements of the base having a magnetic function (protuberance or layer) and the part of the plug having a magnetic function are intended to exert an attractive magnetic force on one another.

The elements of the base having a magnetic function are formed from a ferromagnetic material or a magnetized material.

If the base comprises a layer having a magnetic function, this layer is preferably thin, or even flexible.

The layer of the base having a mechanical function serves as a support for a plurality of protuberances. It is preferably thin, or even flexible.

Any one of the protuberances is intended to be inserted in the cavity of the plug and to thereby prevent accidental disconnection due to lateral forces, i.e., forces in the plane of the base.

The height of the protuberances is great enough for them to perform their lateral maintaining function of the plug. Advantageously, the height of the protuberances is comprised between 0.1 mm and 5 mm, preferably between 0.5 mm and 2 mm.

The surface density of protuberances on the base is high enough to allow a quick connection with no visual inspection.

This is facilitated by the action of the magnetic forces. However, this density of protuberances makes it possible to obtain a connection with no visual inspection, even in the absence of parts performing a magnetic function inside the connector.

However, in the presence of parts performing a magnetic function, one can see that a small lateral movement of the plug near the surface of the base suffices for the magnetic forces to begin their action and assemble the two parts of the connector, causing the insertion of one of the protuberances of the base into the cavity of the plug.

In other words, the high surface density of potential connection zones (the protuberances of the base), combined with the action of the magnetic forces, facilitates a quick connection with no visual inspection.

Advantageously, the diameter of the protuberances (considering cylindrical protuberances) is comprised between 0.1 mm and 10 mm, preferably between 0.5 mm and 5 mm.

Advantageously, the center-to-center distance between two adjacent protuberances is comprised between 1.5 times the diameter and 10 times the diameter, preferably between 1.5 times the diameter and 5 times the diameter.

Advantageously, the protuberances of the base are distributed uniformly over the surface of the base.

If the base is intended for a device worn in the form of a patch, the sum of the surfaces occupied by the protuberances advantageously corresponds to more than 1% of the total surface of the patch, and preferably more than 5% of the total surface of the patch.

Furthermore, in all of these forms, the plug comprises:
a cavity,
a part having an electrical function (i.e., a part made from an electrically conductive material),
a part having a magnetic function (i.e., a part made from a ferromagnetic material or a magnetized material).

A same part in the plug can perform both an electrical and magnetic function.

Figure 21A:
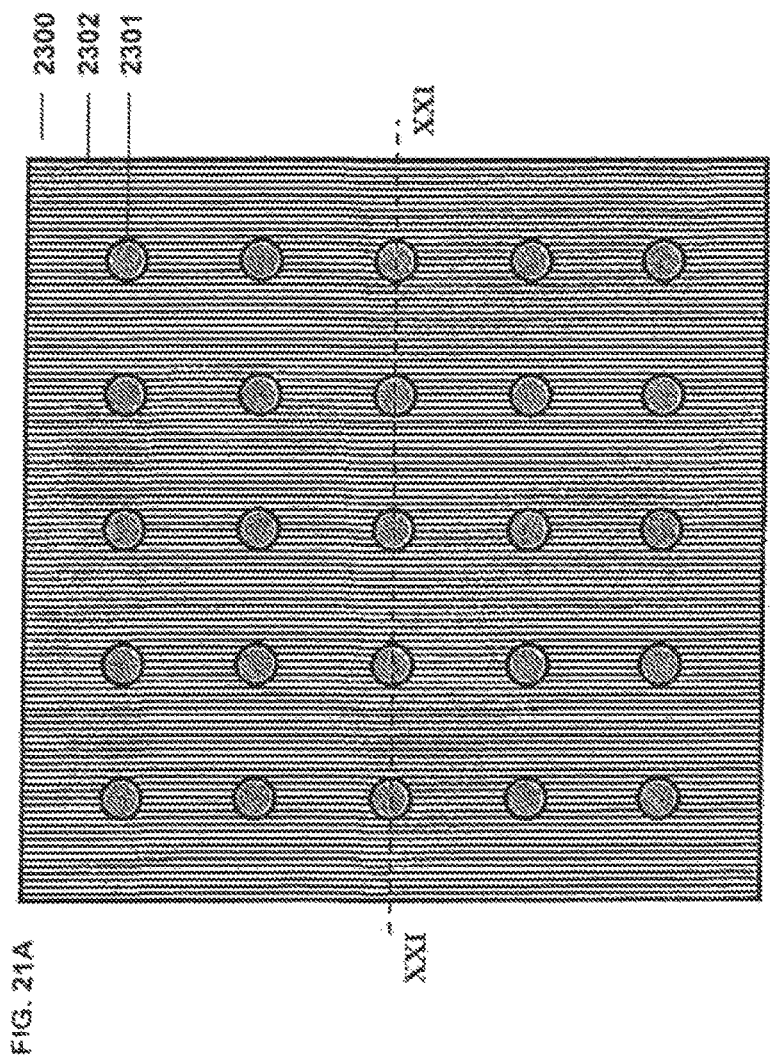

In reference first to FIGS. 21 and 22, FIGS. 21A (top view) and 21B (sectional view along line XXI-XXI in FIG. 21A) show the base 2300 of the electrical connector.

The base 2300 comprises a plurality of protuberances 2301 (here forming a periodic network), an intermediate layer 2302 having an electrical and magnetic function, and a lower layer 2303 having a mechanical function.

The protuberances 2301 are for example made from metal. The intermediate layer 2302 is for example a flexible sheet of magnetic stainless steel. The lower layer 2303 is for example a flexible layer of polymer or a textile material.

FIGS. 22A (top view) and 22B (sectional view along line XXII-XXII in FIG. 22A) show the plug 2200 of the electrical connector.

The plug 2200 comprises a cylindrical part 2201 having an electrical and magnetic function defining a cavity 2203 that is closed by a cylindrical part 2202 forming the base of the plug.

The two cylindrical part 2201 and 2202 are centered around a same axis.

The part 2201 is for example a part made from aluminum-nickel-cobalt, or samarium-cobalt, or neodyme-iron-boron, which are magnetized electrically conductive materials. The part 2202 is for example a metal part.

Figure 21B:
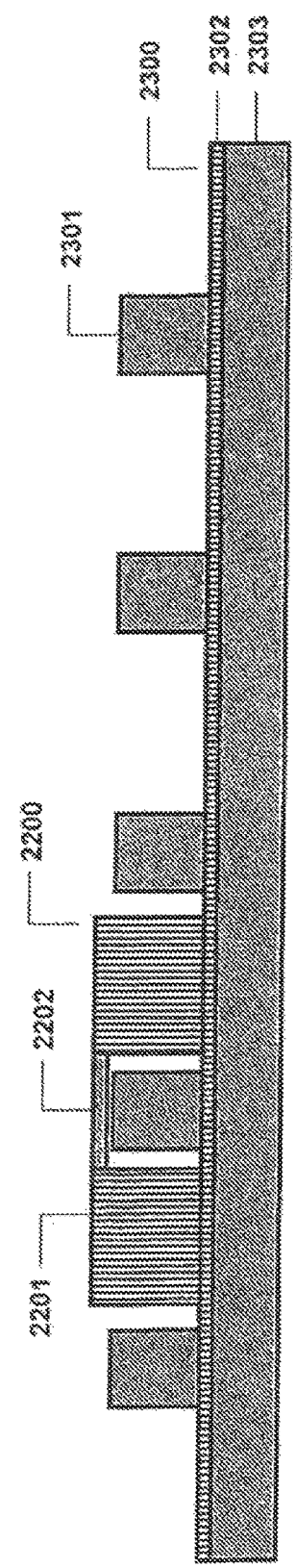

FIG. 21B also shows the plug 2200 once connected to the base 2300.

One of the protuberances 2301 is inserted into the cavity 2203, which prevents accidental disconnection due to lateral forces, i.e., forces in the plane of the base 2300.

The intermediate layer 2302 establishes electrical contact with the part 2201. The intermediate layer 2302 and the part 2201 exert an attractive magnetic force on one another.

In reference now to FIGS. 23 and 24, FIGS. 23A (top view) and 23B (sectional view along line XXIII-XXIII in FIG. 23A) show the base 26 of the electrical connector.

The base 2600 comprises a plurality of protuberances 2601 (here forming a periodic network) having an electrical and magnetic function, and a lower layer 2602 having a mechanical function.

The protuberances 2601 are for example made from magnetic stainless steel. The lower layer 2602 is for example a flexible layer of polymer or textile material.

FIGS. 24A (top view) and 24B (sectional view along line XXIV-XXIV in FIG. 24A) show the plug 2500 of the electrical connector.

The plug 2500 comprises a cylindrical part 2501 and a cylindrical part 2502 forming the base of the plug and having an electrical and magnetic function.

The part 2502 forms, with the part 2501, a cavity 2503. The two cylindrical part 2501 and 2502 are centered around a same axis.

The part 2501 is for example a part made from metal. The part 2502 is for example a part made from aluminum-nickel-cobalt, or samarium-cobalt, or neodyme-iron-boron, which are magnetized electrically conductive materials.

FIG. 23B also shows the plug 2500 once connected to the base 2600.

One of the protuberances 2601 is inserted into the cavity 2503, which prevents accidental disconnection due to lateral forces, i.e., forces in the plane of the base 2600.

The protuberance 2601 establishes electrical contact with the part 2502. The protuberance 2601 and the part 2502 exert an attractive magnetic force on one another.

Figure 25A:
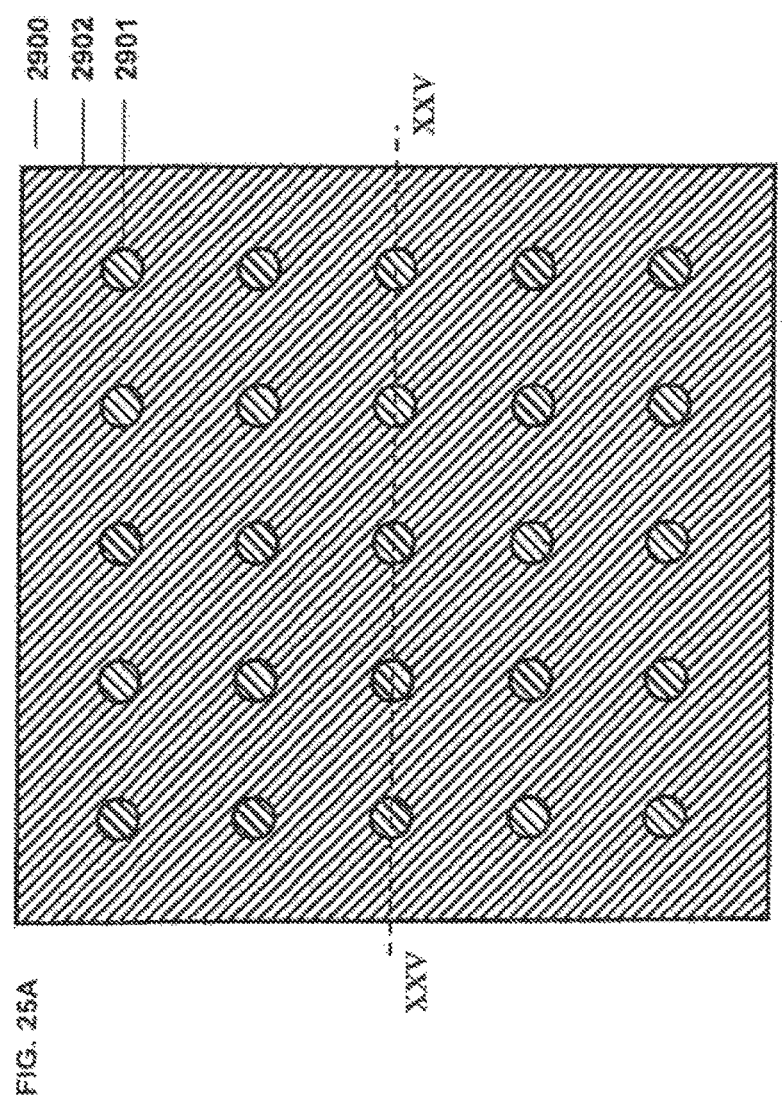

In reference lastly to FIGS. 25 and 26, FIGS. 25A (top view) and 25B (sectional view along line XXV-XXV in FIG. 25A) show the base 2900 of the electrical connector.

The base 2900 comprises a plurality of protuberances 2901 (here forming a periodic network) having a magnetic function, an intermediate layer 2902 having an electrical function, and a lower layer 2903 having a mechanical function.

The protuberances 2901 are for example made from magnetic stainless steel. The intermediate layer 2902 is for example a flexible copper sheet. The lower layer 2903 is for example a flexible layer made from a polymer or textile material.

FIGS. 26A (top view) and 26B (sectional view along line XXVI-XXVI in FIG. 26A) show the plug 2800 of the electrical connector.

The plug 2800 comprises a cylindrical part 2801 having an electrical function, and another cylindrical part 2802 forming the base of the plug and having a magnetic function. The part 2802 forms, with the part 2801, a cavity 2803. The two cylindrical parts 2801 and 2802 are centered around a same axis.

The part 2801 is for example a metal part. The part 2802 is for example a part made from ferrite, or aluminum-nickel-cobalt, or samarium-cobalt, or neodyme-iron-boron, which are magnetized materials.

Figure 25B:
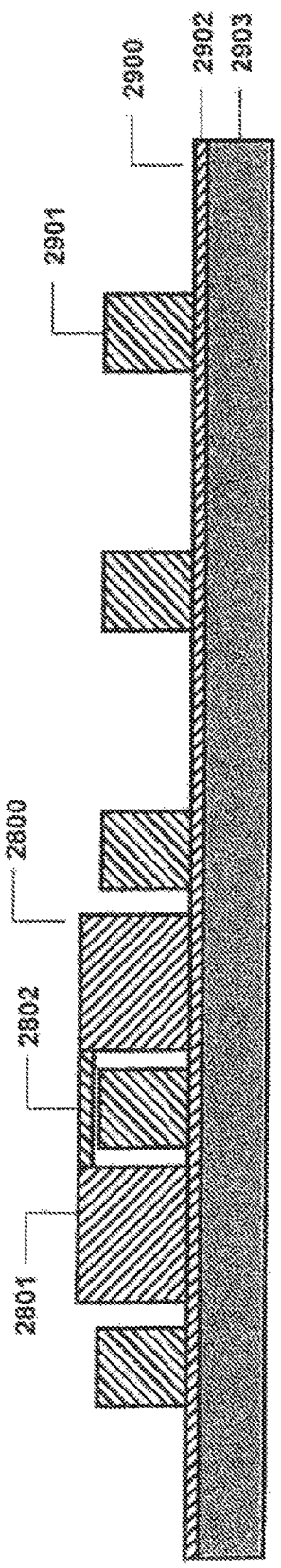

FIG. 25B also shows the plug 2800 once connected to the base 2900. One of the protuberances 2901 is inserted into the cavity 2803, which prevents accidental disconnection due to lateral forces, i.e., forces in the plane of the base 2900. The intermediate layer 2902 establishes electrical contact with the part 2801. The protuberance 2901 and the part 2802 exert an attractive magnetic force on one another.

Throughout the preceding description, the connector according to the disclosure includes a plug. However, the disclosure is not limited to this embodiment. The connector could include several plugs intended to be connected in the same base. The number of plugs will, however, be strictly lower than the number of connecting means provided in the base.

The reference signs inserted after the technical features appearing in the claims are intended solely to facilitate the understanding of the latter and cannot limit the scope thereof.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. An electrical connector for a medical device configured to be fixed on the skin of a user, comprising:
   a base secured to the device; and
   a plug configured to be secured to an electrical conductor, wherein the plug comprises first connection means and the base comprises second connection means configured for cooperating with the first connecting means of the plug to ensure the connection between the base and the plug,
   wherein the base includes a plurality of protuberances and a continuous support layer on which the protuberances are formed,
   wherein the plug includes a cavity for receiving any one of the protuberances when connecting the plug to the base, and
   wherein a number of plugs is less than a number of the protuberances of the base.

2. The connector of claim 1, wherein the base comprises at least one mechanical support layer performing a mechanical support function and the plurality of protuberances is made directly on the support layer that is the mechanical support layer or an intermediate layer, wherein the protuberances, the layer performing a mechanical support function or the intermediate layer perform an electrical function and optionally a magnetic function, and the plug comprises a cylindrical part defining the cavity that is closed by a base, the electrical function of the plug being performed by the cylindrical part or the base and the potential magnetic function of the plug being performed by the cylindrical part or the base.

3. The connector of claim 2, wherein the base comprises, on the layer performing the mechanical support function, the intermediate layer, wherein the electrical function and the potential magnetic function are performed by the mechanical support layer or the intermediate layer, the protuberances being made on the mechanical support layer or on the intermediate layer, the electrical function and the potential magnetic function of the plug being performed by the cylindrical part.

4. The connector of claim 2, wherein the base comprises, on the layer performing the mechanical support function, protuberances being made directly on this mechanical support layer, said protuberances performing the electrical function and optionally a magnetic function, the electrical function and the potential magnetic function of the plug being performed by the base.

5. The connector according to claim 2, wherein the base comprises, on the layer performing the mechanical support function, the intermediate layer performing the electrical function, the protuberances being made on this intermediate layer and optionally performing the magnetic function, wherein the cylindrical part of the plug are configured for performing the electrical function and its base optionally performing the magnetic function.

6. The connector according to claim 5, wherein the protuberances perform the electrical function and the intermediate layer performs a magnetic function.

* * * * *